United States Patent [19]
Meyer et al.

[11] Patent Number: 5,869,336
[45] Date of Patent: Feb. 9, 1999

[54] RECOMBINANT ENZYMATICALLY ACTIVE CALPAIN EXPRESSED IN A BACULOVIRUS SYSTEM

[75] Inventors: Sheryl L. Meyer, Collegeville; Richard W. Scott, Wallingford, both of Pa.; Robert Siman, Wilmington, Del.

[73] Assignee: Cephalon, Inc., West Chester, Pa.

[21] Appl. No.: 896,116

[22] Filed: Jul. 17, 1997

Related U.S. Application Data

[60] Continuation of Ser. No. 454,855, May 31, 1995, abandoned, which is a division of Ser. No. 275,683, Jul. 15, 1994.

[51] Int. Cl.$^6$ .............................. C12N 5/10; C12N 15/63
[52] U.S. Cl. ........................................ 435/348; 435/320.1
[58] Field of Search ................................ 435/320.1, 348, 435/219, 226

[56] References Cited

U.S. PATENT DOCUMENTS 5,322,774   6/1994   Peakman et al. ...................... 435/69.1

OTHER PUBLICATIONS

Alberts, B. et al., "Molecular Biology of the Cell", 2nd edition, Garland Publishing, Inc., New York, 1989, p. 301.

Angermann, A. et al., "Purification and characterization of human salivary–gland prokallikrein from recombinant baculovirus–infected insect cells", *Eur. J. Biochem* 1992, 206, 225–233.

Aoki, K. et al., Complete amino acid sequence of the large subunit of the low–Ca$^2$–requiring form of human Ca$^{2+}$–activated neutral protease ($\mu$CANP) deduced form its cDNA sequence, *FEBS Letters* 1986, 205, 313–317.

Astermark, J. et al., "Baculovirus–mediated expression of the epidermal growth factor–like modules of human factor IX fused to the factor XIIIa transamidation site in fibronectin", *J. Biol. Chem.* 1994, 269(5), 3690–3697.

Barber, G.N. et al., "Detection of protein kinase homologues and viral RNA–binding domains utilizing polyclonal antiserum prepared against a baculovirus–expressed ds RNA–activated 68,000–Da protein kinase", *Virology* 1992, 191, 670–679.

Blanco, G. et al., "Functional expression of the $\alpha 2$ and $\alpha 3$ isoforms of the Na, K–ATPase in baculovirus–infected insect cells", *Proc. Natl. Sci. USA* 1993, 90, 1824–1828.

Boose, J.A. et al., "Synthesis of a human lysosomal enzyme, $\beta$–hexosaminidase B, using the baculovirus expression system", *Protein Expr. Purif.* 1990, 1(2), 111–120.

Burns, D.J. et al., "Expression of the $\alpha$, $\beta$II, and $\tau$ protein kinase–C isozymes in the baculovirus–insect cell expression system", *J. Biol. Chem.* 1990, 265(20), 12044–12051.

Button, L.L. et al., "Recombinant leishmania surface glycoprotein GP63 is secreted in the baculovirus expression system as a latent metalloproteinase", *Gene* 1993, 133, 75–81.

Chen, W. et al., "high level expression of mammalian protein farnesyltransferase in a baculovirus system", *J. Biol. Chem.* 1993, 268(13), 9675–9680.

Cleland, J.L. and Craik, C.S., eds., "Insect cell expression technology", *Principles and Practice of Protein Engineering*, John Wiley & Sons, New York, 1–40 (1996).

Croall, et al., "Comparison of two calcium–dependent proteinases from bovine heart", *Biochem. Biophys. Acta.* 1984, 788, 348–355.

DeLuca, C.I. et al., "Molecular cloning and bacterial expression of cDNA for rat calpain II 80 kDa subunit", *Biochim, Biophys. Acta* 1993, 1216, 81–83.

DeTomaso, A.W. et al., "Expression, targeting, and assembly of functional Na, K–ATPase polypeptides in baculovirus–infected insect cells", *J. Biol. Chem.* 1993, 268(2), 1470–1478.

Fertig, G. et al., "Biotechniological aspects of the production of human pro–kallikrein using the AcNPV–baculovirus–expression system", *Cytotechnology* 1993, 11, 67–75.

Figueiredo–Pereira, M. et al., "Expression of the Largest Subunit of the Bovine Multicatalytic Proteinase Complex (Proteasome) in Insect Cells and in *E. Coli*", *FASEB Journal* 1994, 8(7), A1370.

Graham–Siegenthaler, K. et al., "Active Recombinant Rat Calpain II", *The J. of Biol. Chem.* 1994, 269(48), 30457–30460.

Hasemann, C.A. et al., "High–level production of a functional immunoglobulin heterodimer in a baculovirus expression system", *Proc. Natl. Acad. Sci. USA* 1990, 87, 3942–3946.

Hatanaka, M. et al., "Calpain I, a low Ca$^2$–requiring protease, from human erythrocytes: Purificatin and subunit structure", *Biomed. Res.* 1983, 4(4), 381–388.

Hirowatari, Y. et al., "Two proteinase activities in HCV polypeptide expressed in insect cells using baculovirus vector", *Arch. Virol.* 1993, 133, 349–356.

Imajoh, S. et al., "Molecular cloning of the cDNA for the large subunit of the high–Ca$^{2+}$–requiring form of human Ca$^{2+}$–activated neutral protease", *Biochemistry* 1988, 27, 8122–8128.

Inomata, M. et al., "Activation mechanism of calcium–activated neutral protease", *J. Biol. Chem.* 1988, 263(36), 19783–19787.

Iwamoto, N. et al., "Localization of calpain immunoreactivity in senile plaques and in neurones undergoing neuofibrillary degeneration in Alzheimer's Disease", *Brain Research* 1991, 561, 177–180.

(List continued on next page.)

*Primary Examiner*—Kawai Lau
*Attorney, Agent, or Firm*—Woodcock Washburn Kurtz MacKiewicz & Norris LLP

[57] ABSTRACT

The present invention is directed to mammalian enzymatically active calpain produced in insect cells by recombinant means. Recombinant vectors and baculoviruses containing cDNA encoding the 80 kDa subunit, 30 kDa subunit, and both subunits are described. Methods for producing recombinant enzymatically active mammalian calpain are also described.

9 Claims, 8 Drawing Sheets

OTHER PUBLICATIONS

Kendler, D.L. et al., "Expression of human thyroid peroxidase in insect cells using recombinant baculovirus", *Mol. Cell. Endocrinology* 1993, 93, 199–206.

Kidd, M. et al., "The use of baculovirus as expression vectors", *Applied Biochem. and Biotech.* 1993, 42, 137–159.

Kikuchi, T. et al., "Reconstitution of calpain I and calpain II from their subunits: interchangeability of the light subunits", *Arch. Biochem. Biophys.* 1984, 234, 639–643.

Kitahara, A. et al., "Large–scale purification of porcine calpain I and calpain II and comparison of proteolytic fragments of their subunits", *J. Biochem.* 1984, 95, 1759–1766.

Latchinian–Sadek, L. et al., "Expression, purification, and characterization of the yeast KEX1 gene product, a polypeptide precursor processing carboxypeptidase", *J. Biol. Chem.* 1993, 268(1), 534–540.

Lee, I.J. et al., "Recombinant thyroid hormone receptor and retinoid X receptor stimulate ligand–dependent tanscription in vitro", *Proc. Natl. Acad. Sci.* 1994, 91, 1647–1651.

Lee, K. et al., "Ihibition of proteolysis protects hippocampal neurons from ischemis", *Proc. Natl. Acad. Sci. USA* 1991, 88, 7233–7237.

Luckow, V.A., "Insect cell expression technology", *Principles and Practice of Protein Engineering* 1994, 1–40.

Luckow, V.A., "Baculovirus system for the expression of human gene products", *Current Opinion in Biotechnology* 1993, 4, 564–572.

Luckow, V.A. et al., "High level expression of nonfused foreign genes with autographa californica nuclear polyhedrosis virus expression vectors", *Virology* 1989, 170, 31–39.

Meyer, S.L. et al., "Production and characterization of recombinant mouse brain–derived neurotrophic factor and rat neurotrophin–3 expressed in insect cells", *J. Neurochemistry* 1994, 62(3), 825–833.

Murachi, T., "Calpain and calpastatin", *TIBS* 1983, 8, 167–169.

Ohno, et al., "Nucleotide sequence of a cDNA coding for the small subunit of human calcium–dependent protease", *Nucleic Acids Research* 1986, 14, 5559.

Oliver, S.G. and Ward, J.M., eds., *A Dictionary of Genetic Engineering*, Cambridge University Press, Cambridge 1988.

Patel, G. et al., "Expression of a functional protein kinase C–τ using a baculovirus vector: purification and characterization of a single potein kinase C iso–enzyme", *Cellular Signaling* 1989, 1(3), 227–240.

Rahmatullah, M. et al., "Direct interaction of the $\alpha$ and $\tau$ subunits of the G proteins", *J. Biol. Chem.* 1994, 269(5), 3574–3580.

Rami, A. et al., "Protective effects of calpain inhibitors against neuronal damage caused by cytotoxic hypoxia in vitro and ischemia in vivo", *Brain Research* 1993, 609, 67–70.

Saido, T.C. et al., "Autolytic transition of $\mu$–calpain upon activatio as resolved by antibodies distinguishing between the pre– and post–autolysis forms", *J. Biochem.* 1992, 111, 81–96.

Saito, K.I. et al., "Widespread activation of calcium–activated neutral proteinase (calpain) in the brain in Alzheimer Disease: a potential molecular basis for neuronal degeneration", *Proc. Natl. Acad. Sci. USA* 1993, 90, 2628–2632.

Sambrook, et al., "Molecular Cloning: a laboratory manual", Cold Spring Harbor Laboratory Press, Cold Spring Harbor, NY, (second edition), (1989), 1–1626.

Sasaki, T. et al., "Comparative specificity and kinetic studies on porcine calpain I and calpain II with naturally occurring peptides and synthetic fluorogenic substrates", *J. Biol. Chem.* 1984, 259(20), 12489–12494.

Seubert, P. et al., "Lesions of entorhinal cortex produce a calpain–mediated degradation of brain spectrin in dentate gyrus. I. Biochemical Studies", *Brain Res.* 1988, 459, 226–232.

Siman, R. et al., "Proteolytic processing of β–amyloid precursor by calpain I", *J. Neurosci.* 1990, 10, 2400–2411.

Siman, R. et al., "Role of calpain I in excitatory amino acid–induced degenerative structural changes", *Neuro. of Excutatory Ammo Acids* 1990.

Sorimachi, et al., "Muscle–specific calpain, p94 is degraded by autolysis immediately after translation, resulting in disappearance form muscle", *Journal of Biological Chemistry* 1993, 268(11), 10593–10605.

Sorimachi, H. et al., "New Era of Calpain Research—Discovery of Tissue–Specific Calpains", *FEBS Letters* 1994, 343, 1–5.

Summers, M.D. et al., "A manual of methods for baculovirus vectors and insect cell culture procedures", *Texas Agricultural Experiment Station Bulletin* 1987, 1555, 1–57.

Towbin, H. et al., "Electrophoretic transfer of proteins from polyacryylamide gels to nitrocellulose sheets: procedure and some applications", *Proc. Natl. Acad. Sci. USA* 1979, 76, 4350–4354.

Vaughn, J.L. et al., "The establishment of two cell lines from the insect spodoptera frugiperda (lepidoptera; noctuidae", *In Vitro* 1977, 13, 213–217.

Vernet, T. et al., "Secretion o ffunctional papain precursor from insect cells", *J. Biol. Chem.* 1990, 265(27), 16661–16666.

Vihko, P. et al., "Rat acid phosphatase: overexpression of active, secreted enzyme by recombinant baculovirus–infected insect cells, molecular properties, and crystallization", *Proc. Natl. Acad. Sci. USA* 1993, 90, 799–803.

Wang, X.–M. et al., "Production of Active Human Interleukin–1β–Converting Enzyme in a Baculovirus Expression System", *Gene* 1994, 145, 273–277.

Weyer, U. et al., "Analysis of the promoter of the autographa californica nuclear polyhedrosis virus p10 gene", *J. Gen. Virol.* 1991, 70, 203–208.

Whitefleet–Smith, J. et al., "Expression of human plasminogen cDNA in a baculovirus vector–infected insect cell system", *Archives of Biochem. Biophysics* 1989, 271(2), 390–399.

Wippler, J. et al., "The integrin $\alpha_{IIb}$–$\beta_3$, platelet glycoprotein IIb–IIIa, can form a functionally active heterodimer complex withhout the cysteine–rich repeats of the $\beta_3$ subunit", *J. Biol. Chem.* 1994, 269(5), 8754–8761.

Yamauchi, Y. et al., "Recombinant and native zymogen forms of human complement factor $D^1$", *J. Immun.* 1994, 152, 3645–3653.

Zimmerman, U. et al., "Two stages autolysis of the catalytic subunit initiates activation of calpain–I", *Biochem. Biophys. Acta* 1992, 1078, 192–198.

Delphin, C. et al. (Jil. 1994) "Characterization of baculovirus recombinant wild–type p53. Dimerization of p53 is required for high–affinity DNA binding and cysteine oxidation inhibits p53 DNA binding" Eur. J. Biochem. 223(2):683–692, abstract only.

Hink, W.F., "A serum–free medium for the culture of insect cells and production of recombinant proteins", *In vitro Cellular and Developmental Biology* 27A:397–401 (1991).

DeLuca, C.I. (1992) "Cloning, construction and expression of the cDNA for the large subunit of rat calpain II, and mapping of the gene" *Masters Abstr. Int'l.* 32(1):184.

Fraser, M.J. (1992) "The baculovirus–infected insect cell as a eukaryotic gene expression" *Curr. Top. Microbiol. Immunol.* 158:131–172.

Tian, P. et al. "The nonstructural glycoprotein of rotavirus affects intracellular calcium levels" Journal of Virology (Jan. 1994), vol. 68, No. 1, pp. 251–257.

Hu, Y. et al. "Ca2+ signalling in Sf9 insect cells and the functional expression of a rat brain M5 muscarinic receptor" American Journal of Physiology (Jun. 1994), vol. 266, No. 6, part 1, pp. C1736–C1743.

Saido, T.C. et al. "In situ capture of micromolar–calpain activation in platelets" The Journal of Biological Chemistry (Apr. 1992), vol. 268, No. 10, pp. 7422–7426.

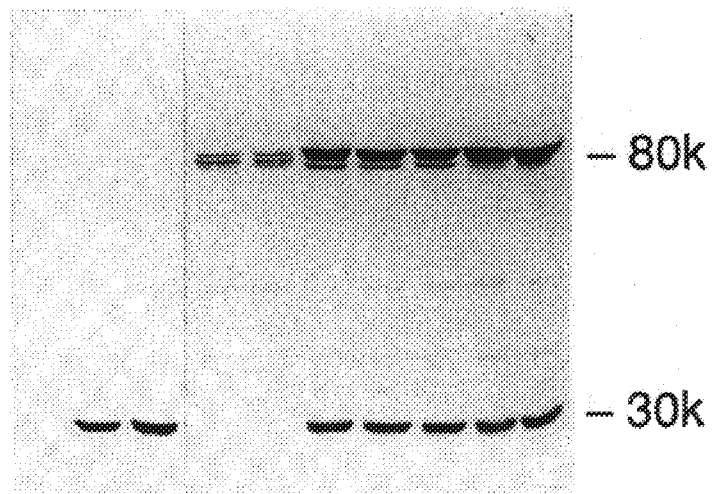
FIG.4
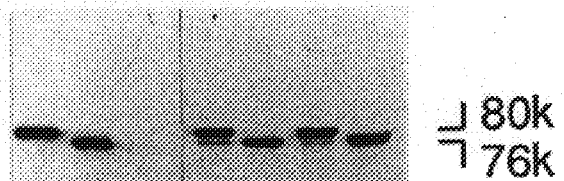
FIG.6
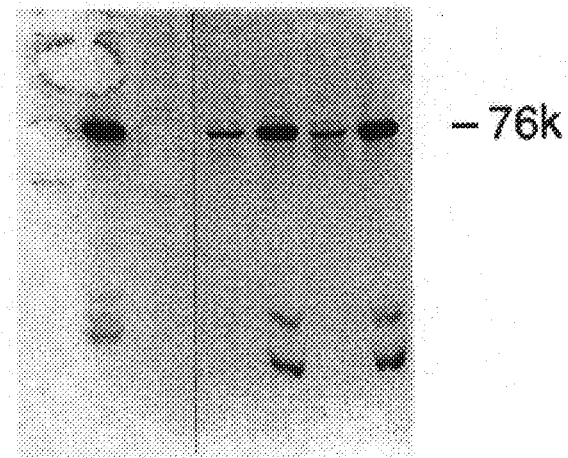

—○— $-Ca^{2+}$
····◆···· $+Ca^{2+}$
--⊞-- $+Ca^{2+}/+INHIB$

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:1:

CGGGATCCTT AGGAATACAT AGTCAGCTGC AGCC     3 4

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

CACCCTGATC TGAAGAC                                          17

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

GTACACTTGA AGCGTGACTT C                                    21

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:4:

CAGGCAGCAA ACGAAATTGT C                                    21

( 2 ) INFORMATION FOR SEQ ID NO:5:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:5:

CGGGATCCTT ATGCAAACAT GGTCAGCTGC AACC                    34

( 2 ) INFORMATION FOR SEQ ID NO:6:

( i ) SEQUENCE CHARACTERISTICS:
        ( A ) LENGTH: 24 base pairs (B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:6:

ATTTGCGGAT GGTCCGGCTC TTGA 24

(2) INFORMATION FOR SEQ ID NO:7:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

CGCGGATCCT ATAAATATGT CGGAGGAGAT CATCACGCCG 40

(2) INFORMATION FOR SEQ ID NO:8:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

CCGGGATCCT ATAAATATGT TCCTGGTT 28

(2) INFORMATION FOR SEQ ID NO:9:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:9:

AACCAGGAAC ATATTTATAG GATC 24

(2) INFORMATION FOR SEQ ID NO:10:

(i) SEQUENCE CHARACTERISTICS:
(A) LENGTH: 21 base pairs
(B) TYPE: nucleic acid
(C) STRANDEDNESS: single
(D) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

GGTGGAACGG CCATGCGCAT C                                                                    2 1

( 2 ) INFORMATION FOR SEQ ID NO:11:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:11:

CATTGATGAT GGAGTCAGGA G                                                                    2 1

( 2 ) INFORMATION FOR SEQ ID NO:12:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:12:

CTGAGAACAG AGCCAAGAGA                                                                      2 0

RECOMBINANT ENZYMATICALLY ACTIVE CALPAIN EXPRESSED IN A BACULOVIRUS SYSTEM

This is a continuation, of application Ser. No. 08/454,855, filed May 31, 1995, now abandoned, which is a divisional of Ser. No. 08/275,683 filed Jul. 15, 1994, all applications hereby incorporated by reference in their entireties.

FIELD OF THE INVENTION

The present invention relates to recombinant enzymatically active human calpain and its method of preparation using recombinant technology in a baculovirus-insect cell system.

BACKGROUND OF THE INVENTION

A. Calpain

Calpain is a calcium-activated neutral protease, also known as CANP; EC 3.4.22.17. It is an intracellular cysteine protease which is ubiquitously expressed in mammalian tissues (Aoki et al., FEBS Letters 205:313–317, 1986). Calpain has been implicated in many degenerative diseases including, but not limited to, neurodegeneration (Alzheimer's disease, Huntington's disease, and Parkinson's disease), amyotrophy, stroke, motor neuron damage, acute central nervous system (CNS) injury, muscular dystrophy, bone resorption, platelet aggregation, and inflammation.

Mammalian calpain, including human calpain, is multimeric. It consists of two different subunits, which are a 30 kDa subunit and an 80 kDa subunit, and, therefore, is a heterodimer. There are two forms of calpain, calpain I ($\mu$-calpain, $\mu$CANP) and calpain II (m-calpain, mCANP), which differ in their sensitivities to the concentration of calcium necessary for activation. Calpain I requires only low micromolar concentrations of calcium for activation, whereas calpain II requires high micromolar or millimolar levels (Aoki et al. supra, and DeLuca et al., Biochim. Biophys. Acta 1216:81–83, 1993). The same 30 kDa subunit is common to both forms. The two human calpains differ in the sequences of the DNA encoding their 80 kDa subunit, sharing 62% homology. There is evidence that the 80 kDA subunit is inactive, but that it is autolyzed to a 76 kDa active form in the presence of calcium (Zimmerman et al., Biochem. Biophys. Acta., 1078:192–198, 1991).

R. Siman, in Neurotoxicity of Excitatory Amino Acids, A. Guidotti, ed., Raven Press, Ltd., New York (1990) reported upon the role of calpain I in excitatory amino acid (EAA) induced neurotoxicity, eventually leading to neuronal cell death. Siman advanced the proposition that calpain I activation is an early event in the neurodegenerative process and not just a secondary response to neuronal death. Siman further reported that only one highly selective blocker of calpain was available at that time—calpastatin. However, calpastatin is not readily taken up by cells, as it is a large globular protein of approximately 280 kDa. Siman also reported that protease inhibitors of broader specificity, including leupeptin, were unsuccessful in lowering EAA-induced protein breakdown in vivo. Leupeptin was ineffective presumably because it failed to enter the cells.

Iwamoto et al., Brain Research, 561:177–180 (1991), described that activation of calpain may be an important factor in the abnormal proteolysis underlying the accumulation of plaque and tangles in brain tissue from people who suffered Alzheimer-type dementia.

Saito et al., Proc. Natl. Acad. Sci. USA, 90:2628–2632 (1993) reported that synaptic loss and neuronal cell death correlate strongly with the degree of cognitive impairment in Alzheimer's disease. They also reported that calpain I was significantly activated in human postmortem brain from patients with Alzheimer's disease, and that the degree of activation correlated with those regions of the brain showing the greatest amount of degeneration. It was suggested that the influences of calpain activation may contribute to neurofibrillary pathology and abnormal amyloid precursor protein processing prior to causing synapse loss or cell death in the most vulnerable neuronal populations. Because of the association between calpain and nerve degeneration diseases, pharmacological modulation of the calpains by inhibitors merits consideration as a potential therapeutic strategy in such diseases, for example, in Alzheimer's disease.

Rami et al., Brain Research, 609:67–70 (1993) reported that both calpain inhibitor I and leupeptin protected neurons against ischemic and hypoxic damage resulting from ischemia induced by clamping both carotid arteries and lowering the arterial blood pressure of rats.

Lee et al., Proc. Natl. Acad. Sci. USA, 88:7233–7237 (1991) provide evidence that calcium-activated proteolysis is an important event in the process of post-ischemic cell death and they reported that inhibition of calcium-activated proteolysis by means of the proteolytic inhibitor leupeptin protected against the degeneration of vulnerable hippocampal neurons after ischemia. Leupeptin was selected because it was the only protease inhibitor that was previously shown to block a trauma-evoked calpain response in vivo (Seubert et al., Brain Res., 459:226–232, 1988). The authors noted, however, that the therapeutic utility of modulating calcium-activated proteolysis will probably depend on the development of more permeable, potent and specific protease inhibitors.

As evident from the foregoing, specific inhibitors of calpain may provide a means of treating those neurodegenerative diseases in which calpain is implicated. Calpastatin offers limited utility due to its cell impermeability. Protease inhibitors of broader specificities may not function in vivo and/or may have undesirable side-effects. Thus, other calpain inhibitors must be identified, and a ready, convenient, safe source of calpain will promote the search for such inhibitors.

B. Calpain cDNA

Recombinant enzymatically active human calpain for testing for inhibitors offers the advantages of 1) being a considerably more convenient, readily available source of large amounts of enzyme 2) being easier to purify and 3) being free from the safety issues which must be addressed when the source is human tissues, especially human blood cells, i.e., potentially hazardous viruses. Native human calpain is currently isolated from human erythrocytes and can be purified to what the authors characterize as apparent homogeneity (Hatanaka et al., Biomed. Res., 4:381–388, 1983). However, aside from the obvious problems with source, the purification procedure can be quite tedious, due to the low levels of calpain relative to the amount of starting material. Furthermore, native calpain is isolated in the presence of an endogenous inhibitor (calpastatin) which must be separated during purification. A good source of large amounts of enzymatically active calpain would greatly enhance the search for calpain inhibitors by 1) increasing the availability of calpain for use in reproducible assays for calpain inhibitors and 2) by facilitating crystallization of the enzyme, thereby permitting the design of rational inhibitors. A recombinant system for production further facilitates the production of directed mutants to assist in structural studies.

Therefore, a recombinant system for producing active calpain is needed.

The problem in producing enzymatically active calpain by recombinant means is that of expressing two different gene products (the 80 kDa subunit and 30 kDa subunit), getting proper processing and folding of the individual products, and obtaining the proper combination of the two products to produce enzymatically active molecules. As stated in the previous discussion, activated calpain has been implicated in the killing of neuronal cells. Unfortunately, then, any enzymatically active calpain produced in a recombinant system would be expected to be deleterious or lethal to that expression system. Any deleterious effects upon the expression system utilized would be expected to increase as more of the activated product is expressed. Notably, many mammalian cells produce an endogenous inhibitor of calpain, which may exert an important control over the activity of an otherwise lethal protease.

Aoki et al., supra, described the complete amino acid sequence of the 80 kDA subunit of human calpain I ($\mu$CANP) which they deduced from the sequence of a cDNA clone of human calpain. The cDNA clone of human calpain was isolated from the cDNA library from human skeletal muscle using a cDNA for the large subunit of rabbit $\mu$CANP as a probe. Expression of the cDNA is not reported.

Imajoh et al., *Biochemistry*, 27:8122–8128 (1988) described the isolation of a cDNA clone for the large subunit of human calpain II from a human skeletal muscle library probed with chicken CANP and rabbit mCANP. It is reported that the deduced protein had essentially the same structural features as those described for $\mu$CANP and chicken CANP. The amino acid sequence similarities of the human mCANP to human $\mu$CANP and chicken CANP were reported as 62% and 66%, respectively. Expression of the cDNA is not described or suggested.

Ohno et al., *Nucleic Acids Research*, 14:5559 (1986) described the sequence of a cDNA coding for the small subunit (30 kDa) of human calcium activated protease isolated from a human spleen cDNA library. Comparisons with the reported amino acid sequences of rabbit and porcine sequences revealed only 3% differences.

DeLuca et al., supra., reported the molecular cloning and bacterial expression of cDNA for the rat calpain II (mCANP) 80 kDa subunit. The cDNA encodes a protein reportedly exhibiting 93% sequence identity with human calpain II, and 61% identity with human calpain I. Expression of the cDNA was in *E. coli* bacteria in a phagemid expression vector. Because the expressed product was insoluble and inactive after cell sonication, it could not be used to screen for calpain inhibitors.

C. Baculovirus Expression Systems

V. Luckow, *Current Opinion in Biotechnology*, 4:546–572 (1993) and Kidd et al, *Applied Biochem. and Biotech.*, 42:137–159 (1993) recently reviewed baculovirus systems for the expression of human gene products and the use of baculoviruses as expression vectors, respectively. Luckow discussed the production of a number of different kinds of proteins, including enzymes. However, the production of only one proteolytic enzyme is mentioned, namely, the metalloprotease stromelysin. Unlike calpain, this enzyme is not multimeric.

Kidd et al., discussed the use of baculovirus-produced proteins for X-ray structural analysis and for assembly of subunits to form functional multisubunit molecules. A number of examples displayed the proper assembly of the subunits to produce functional molecules. Although the author broadly stated that baculovirus expression results in the structural integrity of the folded molecules and full biological function in virtually all cases, the assembly of subunits of dimeric or multimeric enzymes into a functional enzyme was not reported. Further, in other instances involving multisubunit molecules, i.e. Na,K,ATP-ase, the assembly of subunits was sometimes inefficient. (See DeTomaso et al., infra.)

Others have reported the expression of enzymes in the baculovirus system. Vernet et al., *J. Biol. Chem.*, 27:16661–16666 (1990) described the secretion of a papain precursor from insect cells. Papain is a cysteine protease. The prepropapain gene was cloned into the transfer vector IpDC125 behind the polyhedron promoter. The recombinant construct was incorporated by homologous recombination into the genome of the polyhedrosis virus *Autographa californica*. An enzymatically inactive papain precursor was recovered from *Spodoptera frugiperda* Sf9 cells infected with the recombinant baculovirus. Proper processing of the papain precursor to produce an active enzyme did not occur in the infected cells.

Fertig et al., *Cytotechnology*, 11:67–75 (1993) described the production of pro-kallikrein, which is a precursor of kallikrein, a serine protease. Pro-kallikrein was produced in insect cells from Spodoptera frugiperda (Sf9) and *Mamestra brassicae* (IZD-Mb503) infected with a recombinant nuclear polyhedrosis virus *Autographa californica* (AcNPV), strain E2. To obtain an active enzyme, the pro-kallikrein produced was activated in vitro using trypsin.

Button et al., *Gene*, 133:75–81 (1993) described the production of the metalloproteinase GP63 of *Leishmania major* in a baculovirus-insect cell expression system. The enzyme was secreted from *Spodoptera frugiperda* (Sf9) cells infected with a recombinant nuclear polyhedrosis virus *Autographa californica* (AcNPV) as a latent protease which was subsequently activated to full proteinase activity by means of HgCl2 treatment.

Hirowatari et al., *Arch. Virol.*, 133:349–356 (1993) described the expression of a polypeptide believed to exhibit two viral proteinase activities required for the processing of the viral precursor protein of hepatitis C virus (HCV). The polypeptide was expressed in the insect cell line Sf21 infected with a recombinant baculovirus. Baculovirus transfer vector pVL941 was utilized. The proteinase activities were inferred from the presence of a 70 kDa processed protein.

Although the production of enzymatically active multimeric proteases in the baculovirus system has not, to the inventors' knowledge, been reported, the baculovirus system has been used to express functional, multimeric enzymes other than proteases. DeTomaso et al., *J. Biol. Chem.*, 268(2):1470–1478 (1993) describe the expression of functional, rat Na,K-ATPase using the baculovirus expression system. An expression system using insect cells was chosen because some insect cells have little or no levels of Na,K-ATPase. A baculovirus system was chosen since baculovirus-infected cells produce high levels of foreign protein. Sf-9 cells derived from *Spodoptera frugiperda* were utilized. The baculovirus was *Autographa californica*. However, because the activity of enzyme from insect cells was only 20–25% as great as that from dog kidney outer medulla, the authors concluded that a portion of the enzyme expressed was inactive.

Wen-Ji et al., *J. Biol. Chem.*, 268(13):9675–9680 (1993) describe the expression of functional mammalian protein farnesyltransferase in a baculovirus system using SF9 cells. The specific activity of the expressed protein was 510 nM/mg/hr, which is stated to be essentially identical to that reported for the rat brain enzyme. It was noted, however, that the quantities of protein obtained from native tissue did not previously allow direct assay of the protein concentration, so this is the first time specific activity of the protein was determined using a standard protein assay.

There is no disclosure, or suggestion, of expressing an enzymatically active, multimeric, potentially lethal, protease such as calpain in any expression system. It was expected that expression of calpain I, in particular, would be difficult and would require the presence of an inhibitor, because calpain I is activated at extremely low levels of Ca++ that could be achieved during the infection cycle. Surprisingly, the present inventors unexpectedly found that enzymatically active calpain can be expressed in the baculovirus system, and in the absence of an inhibitor.

SUMMARY OF THE INVENTION

The present invention is directed to the production of enzymatically active mammalian calpain by recombinant means. The production of recombinant enzymatically active human calpain I in a baculovirus-insect-cell system is specifically described. Calpain so produced can be beneficially used in assays for screening potential calpain inhibitors, thus advancing the art by allowing for rapid and efficient selection of calpain inhibitors which can be used to treat those diseases in which calpain has been implicated, and for providing sufficient calpain to be crystallized for the rational design of calpain inhibitors. Calpain so produced can also be used in other applications including as a meat tenderizer and a blood clot dissolver.

In one aspect, the present invention is directed to enzymatically active mammalian calpain produced by recombinant technology.

In another aspect, the present invention relates to plasmid vectors comprising cDNA encoding mammalian calpain for the production of recombinant enzymatically active mammalian calpain.

In yet another aspect, the present invention relates to recombinant baculoviruses comprising cDNA encoding mammalian calpain for the production of recombinant enzymatically active mammalian calpain.

In a further aspect, the present invention relates to a method for producing enzymatically active mammalian calpain by recombinant means using a baculovirus-insect cell system.

BRIEF DESCRIPTION OF THE FIGURES

FIG. 4 depicts the expression of the subunits in Sf21 cells as determined by immunoblot.

FIG. 6, a–b, depicts calcium-dependent processing of the inactive 80 kDa subunit to the 76 kDa active form.

DETAILED DESCRIPTION OF THE INVENTION

Figure 1:
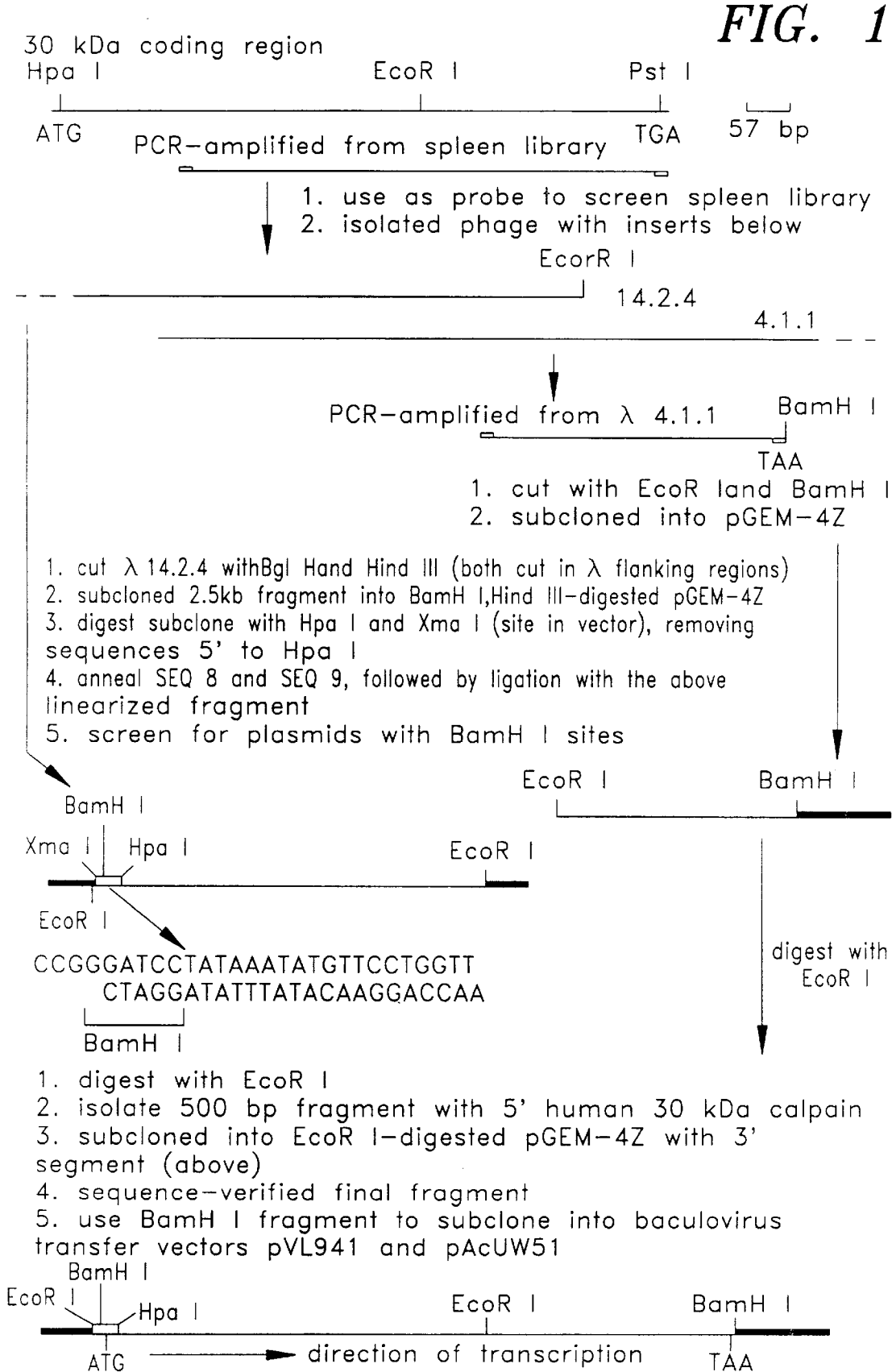
FIG. 1 depicts the cloning strategy for the 30 kDa calpain subunit.

The present invention is directed to the production of mammalian calpain, specifically enzymatically active calpain, by recombinant means. "Calpain" as used herein includes both calpain I and calpain II and refers to the heterodimer consisting of the two subunits. These subunits are the smaller subunit, having a molecular weight of approximately 30 kDa, and the larger subunit, having a molecular weight of approximately 80 kDa, depending on its state of activation. Reference to the 80 kDa subunit includes at least the 77 kDa and 76 kDa forms resulting from autolysis of the 80 kDa subunit. As will be apparent to those skilled in the art, the subunits from the different mammalian species, even the subunits from different tissues of the same mammalian species (Hatanaka, supra), can vary in molecular weight. These variations are included.

"Enzymatically active" as used herein refers to the ability to measurably hydrolyze at least one known substrate of calpain, including calpain itself, i.e., as a result of autolysis. Enzymatic activity can be measured by any means acceptable to those skilled in the art for making such determinations including, but not limited to, fluorescent and calorimetric means. That portion of each subunit sufficient to maintain enzymatic activity as described above is included. The method according to the present invention facilitates the ready determination of those regions of the coding sequence (cDNA) necessary for enzyme activity and the changes in activity which can result upon intentional mutation of the coding sequence. The phrase "enzymatically active upon expression" as used herein refers to calpain, or a subunit thereof, having measurable enzymatic activity upon expression without requiring any manipulation other than the presence of calcium.

"Expression" as used herein includes, but is not limited to, in vitro translation of the cDNA contained in the vectors and viruses according to the invention in insect and other cells. Because some $Ca^{2+}$ is usually present during expression, particularly in the instance of serum-containing medium, the calpain so produced is enzymatically active upon expression.

The term "recombinant" as used herein includes, but is not limited to, a molecule, microorganism, plasmid, phage, or other vector, containing a new combination of DNA sequences. The term "microorganism" includes viruses and bacteria. The terms "plasmid", "phage", and "vector" are used according to their meanings as known to those skilled in the art as defined, for example, in *A Dictionary of Genetic Engineering*, Stephen G. Oliver and John M. Ward, eds., Cambridge University Press, Cambridge, 1988 (incorporated herein by reference).

The term "mammalian" includes all animals of the phylogenetic class "mammalian". Preferably, the calpain is recombinant enzymatically active human calpain. More preferably, the calpain is recombinant enzymatically active human calpain I.

The baculovirus *Autographa californica* nuclear polyhedrosis virus (AcNPV), used in the disclosure that follows, is exemplary. However, other baculoviruses such as *Bombyx mori* nuclear polyhedrosis virus (BmNPV), *Heliothis zea* nuclear polyhedrosis virus, *Lymantria dispar* nuclear polyhedrosis virus, as well as *Orcytes baculoviruses*, viruses of the Poxviridae and Parvoviradae, Choristoneura, and Amsacta can be considered in place of AcNPV. See "Insect Cell Expression Technology", pp 1–40, in *Principles and Practice of Protein Engineering*, Jeffrey L. Cleland & Charles S.

Craik, (Eds.), John Wiley & Sons, 605 Third Avenue, New York, N.Y. 10158-0012.

While cells from the insect *Spodoptera frugiperda* were used to illustrate the present invention, over 400 insect cell lines have been established and can be used, especially those from *Trichoplusia ni*. See Cleland & Craik, supra. Those skilled in the art can readily determine an insect cell suitable for expression. It is also contemplated that other cells, such as yeast and mammalian cells, can be utilized with the appropriate vector, the selection of which is within the skill in the art.

The heterologous genes to be expressed by the baculoviruses are commonly under the control of the polyhedrin or P10 promoters of AcNPV because the polyhedrin and P10 genes are not essential for replication or maturation of the virus and are highly transcribed. This in no way limits the use of other promoters for the practice of this invention. See Cleland & Craik, supra.

The expression and recovery of recombinant enzymatically active calpain is specifically disclosed. This was unexpected, particularly for calpain I, which is activated in the presence of micromolar amounts of calcium because $Ca^{2+}$ is present in the tissue culture medium in which the cells used for its production are grown. Because infected cells generally become "leaky", it was expected that $Ca^{2+}$ would enter the cells from the surrounding medium in sufficient quantity to activate any calpain I produced which, in turn, would be lethal for the cells and would cause the calpain I to digest itself by autolysis.

The recombinantly produced calpain has been determined to be fully enzymologically active and to have an enzyme activity profile similar to that of native calpain, which is important for the use of such recombinantly derived calpain in the screening of potential therapeutic calpain inhibitors. The recombinantly produced calpain exhibited similar sensitivity to known calpain inhibitors, and lack of sensitivity to inhibitors of serine or aspartic protease. The amount of calcium required to achieve ½ $V_{max}$ was essentially the same for both native and recombinant calpain. Similarly, the rates of substrate hydrolysis were similar, as were the specific activities (data not shown). Again, these features are important for full exploitation of the calpain according to the invention.

Surprisingly, the specific activity of the 80 kDa 30 subunit alone was determined to be approximately 20–25% that of the heterodimer. The specific activity of the 80 kDa subunit dissociated from the native heterodimer was previously determined to be only 3% of the heterodimer. (Kikuchi et al. *Arch. Biochem. Biophys.*, 234: 639–645, 1984). Thus, the structure of the recombinantly produced 80 kDa subunit appears to be different than that of the subunit dissociated from native calpain, and may more closely represent the structure of the active subunit. The recombinant production of the calpain subunits, therefore, facilitates the study of structure of the individual subunits.

In the present invention, the expression of calpain was achieved by the expression of both the 80 kDa and 30 kDa subunits in the same insect cells by either co-infecting cells with two separate viruses comprising a cDNA for each subunit of calpain, or infecting the insect cells with a single virus comprising cDNA for both subunits. It was also discovered that an increased amount of the 80 kDa subunit is expressed when the 30 kDa subunit is coexpressed, thus the 30 kDA subunit may have a stabilizing effect on the 80 kDA subunit.

When cells are infected with viruses containing both calpain subunits, all infected cells should express both subunits. Regardless of the added multiplicity of infection (MOI), when cells are infected with virus containing only one subunit or the other, a higher MOI is required to achieve expression of both subunits, e.g., an MOI of 5 for each virus is needed for 99% of the cells to contain one or more particles of both viruses and, thus, express both subunits. In a preferred embodiment, expression is effected by coexpression of both subunits in a single cell.

To construct the recombinant calpain baculoviruses, probes for part of the coding regions of both the 30 kDa and the 80 kDa subunits were prepared by polymerase chain reaction (PCR) from a cDNA library and were used to screen a human cDNA phage library. Phages containing most of each subunit's coding region were isolated and the insert DNA subcloned. Any regions not present in the isolated clones were PCR-amplified from the library, sequence-verified, and attached to the partial clones to produce the entire calpain coding region. The human cDNA library chosen was a spleen library available from Clontech (Palo Alto, Calif., #HL1134a). A spleen library was chosen based on the reported abundant expression of calpain I and II in rat spleen (Murachi, *Trends Biochem. Sci.* 8:167–169, 1983).

Table I lists the synthetic oligonucleotide primers used for the amplification of portions of the human calpain 80 kDa and 30 kDa subunits. Primers were selected based on the published cDNA sequences for the 80 kDa subunit of calpain I (Aoki et al., *FEBS Lett.* 205:313–317, 1986, incorporated herein by reference) and the 30 kDa subunit (Ohno et al., *Nucl. Acids Res.* 14:5559, 1986, incorporated herein by reference). Primers for the 80 kDa subunit of calpain I were further chosen based on their dissimilarity to the related human calpain II and primers for the calpain II 80 kDA subunit were chosen based on their dissimilarity to human calpain I. Internal primers were selected to be just outside of known restriction endonuclease sites, allowing for subsequent digestion at those sites for subcloning the PCR fragments into plasmid vectors. All sequences in Table I are reported 5' to 3'. An "S" following the sequence indicates sense. An "AS" indicates antisense. Primers for the 30 kDa subunit are indicated by "30" and primers for the 80 kDA subunits of calpain I and II are designated "80I" and "80II", respectively. Parentheticals below the sequence identification numbers represent internal laboratory designations and these will be used in the examples to follow.

TABLE I

| Primers Used to Amplify Human Calpain I | | |
|---|---|---|
| SEQ ID NO:1 (SM-36) | CGGGATCCTT AGGAATACAT AGTCAGCTGC AGCC | (AS,30) |
| SEQ ID NO:2 (SM-37) | CACCCTGATC TGAAGAC | (S,30) |
| SEQ ID NO:3 (SM-40) | GTACACTTGA AGCGTGACTT C | (S,80I) |
| SEQ ID NO:4 (SM-41) | CAGGCAGCAA ACGAAATTGT C | (AS, 80I) |
| SEQ ID NO:5 (SM-47) | CGGGATCCTT ATGCAAACAT GGTCAGCTGC AACC | (AS, 80I) |
| SEQ ID NO:6 (SM-49) | ATTTGCGGAT GGTCCGGCTC TTGA | (AS, 80I) |
| SEQ ID NO:7 (SM-53) | CGCGGATCCT ATAAATATGT CGGAGGAGAT CATCACGCCG | (S,80I) |

TABLE I-continued

Primers Used to Amplify Human Calpain I

| SEQ ID NO:8 (SM-65) | CCGGGATCCT ATAAATATGT TCCTGGTT | (S,30) |
| SEQ ID NO:9 (SM-66) | AACCAGGAAC ATATTTATAG GATC | (AS,30) |
| SEQ ID NO:10 (DL-13) | GGTGGAACGG CCATGCGCAT C | (S,30) |
| SEQ ID NO:11 (SM-69) | CATTGATGAT GGAGTCAGGA G | (S,80II) |
| SEQ ID NO:12 (SM-70) | CTGAGAAACA GAGCCAAGAG A | (AS, 80II) |

All polymerase chain reactions were performed in a thermal cycler (Perkin-Elmer, Norwalk, Conn.) using either 2.5 units of Taq DNA polymerase (Promega, Madison, Wis.), 3 units of UlTma DNA polymerase (Perkin-Elmer, Norwalk, Conn.) or 2 units of Tli DNA polymerase (Promega, Madison, Wis.) in the presence of the supplied buffer, 0.2 mM dNTP's (Taq and Tli DNA polymerases) or 40 μM dNTP's (UlTma DNA polymerase), 0.75–2 mM added MgCl$_2$, and 0.25 μM of each primer. After an initial denaturing incubation for 5 minutes at 94° C., 30–35 cycles of amplifications were performed as indicated below, followed by a final extension at 72° C. for 7 minutes. The template was 1–10 μl of lambda phage library, or partially purified phage, added to a minimum of 30 μl of distilled water. DNA was released for amplification by three subsequent freezings in dry-ice ethanol followed by thawing at 37° C.

EXAMPLE 1

Cloning the Human Calpain 30 kDa Subunit

FIG. 1 depicts the strategy for cloning the human calpain 30 kDa subunit. Primers DL-13 5'>GGTGGAACGGCCAT-GCGCATC>3' and SM-36 5'>CGGGATCCTTAGGAATA-CATAGTCAGCTGCAGCC>3' were used to amplify base pairs #163–805 of the human 30 kDa cDNA from the HL1134a human spleen λgt10 library (Clontech Laboratories, Inc., Palo Alto, Calif.) for use as a probe. Base pair (bp) numbering throughout follows from the assignment of the initiation codon "ATG" as base pairs #1–3. Conditions for the PCR were as above using 30 amplification cycles of 1 minute at 94° C., 1 minute at 55° C., and 1 minute at 72° C. The 643-bp fragment was isolated from low-melt agarose after electrophoresis (SeaPlaque-GTG, FMC BioProducts, Rockland, Me.) and purified by extraction with phenol-chloroform. The fragment was then labeled with [32]P-dCTP (Amersham, Arlington Heights, Ill.) by random-primed labeling using Klenow DNA polymerase following the supplied method (Promega Corp., Madison, Wis.) and used to screen the library as follows.

The library was plated for screening on the C600hfl host supplied by Clontech. Approximately 350,000 plaque-forming units were plated on fourteen, 150 mm diameter petri plates. Duplicate nitrocellulose lifts were prepared from these plates after the procedures described by Sambrook et al., *Molecular Cloning: A Laboratory Manual*, (second edition) p 1–1626, Cold Spring Harbor Laboratory, Cold Spring Harbor, N.Y. Hybridization reactions with the denatured labeled probe were carried out overnight at 68° C. in 6×SSC, 50 mM sodium phosphate, pH 6.8, 10 mg/ml poly A (Sigma Chemical Co., St. Louis, Mo.), 0.2 mg/ml heparin (Sigma Chemical Co., St. Louis, Mo.), and 0.5% SDS, followed by two washes with 3×SSC, 0.1% SDS at room temperature and two washes at 1×SSC, 0.10% SDS for 30 minutes at 55° C. Labeled plaques were detected by autoradiography.

Two phages were found to have inserts containing a portion of the cDNA for the 30 kDa subunit. The entire 5' end of the cDNA, ending with the internal EcoRI site at bp #488, was present in the lambda phage designated 14.2.4. Lambda phage designated 4.1.1 contained most of the protein coding region. Plaque-purified 4.1.1 phage was then used to PCR amplify the 3' end of the cDNA. Primers SM-37 5'>CACCCTGATCTGAAGAC>3' and SM-36 5'>CGG-GATCCTTAGGAATACATAGTCAGCTGCAGCC>3' were used. Primer SM-36 adds a BamHI restriction site immediately 3' to the stop codon and changes the stop codon to "TAA". Amplification was carried out with UlTma DNA polymerase (Perkin-Elmer, Norwalk, Conn.) using the supplied buffer with the addition of 40 μM dNTP's and 0.75 mM added MgCl$_2$ (for 10 μl of phage template; 1.55 mM final Mg$^{2+}$ concentration). The amplification cycles were as follows: 2 minutes denaturation step at 97° C. before addition of the polymerase, followed by 30 amplification cycles of 1 minute at 95° C., 45 seconds at 55° C. and 1 minute at 72° C. The fragment obtained was then digested with EcoRI and BamHI, isolated from low-melt agarose as above and subcloned into EcoRI, BamHI-digested pGEM-4Z (Promega Corp., Madison, Wis.).

The 5' portion of the gene was obtained in two steps. First, DNA isolated from plaque-purified lambda phage 14.2.4 was digested with HindIII, which cuts the lambda DNA in the region 5' to the insert, and BglII, which cuts the lambda DNA in the region 3' to the insert. The resulting 2.5 kb fragment was subcloned into BamHI, HindIII-digested pGEM-4Z. A pair of synthetic oligonucleotides were then used to modify the region 5' to the start codon by both adding a BamHI site to facilitate cloning into the transfer vectors and inserting the sequence CCTATAAAT from the polyhedrin gene 5' untranslated region immediately before the start codon in an attempt to achieve optimal baculovirus translation. The plasmid containing the lambda insert was digested with XmaI, which cuts in the multiple cloning site of the pGEM-4Z vector 5' to the BamHI site, and HpaI, which cuts at base pair #13 in the 30 kDa cDNA, which is 3' to the BamHI site, in order to remove the calpain cDNA sequences 5' to the HpaI site. The digested plasmid was isolated from low-melt agarose as above. Two oligonucleotides, SM-65 5'>CCGGGATCCTATAAATAT-GTTCCTGGTT>3' and SM-66 5'>AACCAGGAA-CATATTTATAGGATC>3' were annealed to one another as shown in FIG. 1 by co-incubation in 10 mM Tris-HCl, pH 7.0, 50 mM NaCl at the following temperatures for 10 minutes each: 90° C., 65° C., 42° C., 37° C., and room temperature. The annealed oligonucleotides were then ligated to the linearized, digested plasmid and the resulting colonies were screened for the presence of the BamHI site that is added by these oligonucleotides (FIG. 1).

The cDNA of the entire coding region was then assembled from the two plasmids described above. The plasmid containing the 5' portion of the cDNA was digested with EcoRI. There is an EcoRI site in the vector multiple cloning region 5' to the XmaI site and also a site at bp #488 in the 30 kDa cDNA. This approximately 500 bp EcoRI fragment containing all the additions to the 5' end of the 30 kDa cDNA was then isolated 20 from low-melt agarose as above and ligated to the EcoRI-digested plasmid containing the 3' portion of the cDNA. A plasmid with the EcoRI fragment in the correct orientation was obtained. Dideoxynucleotide DNA sequencing (Sanger et al., *Proc. Natl. Acad. Sci. USA* 74:5463–5467, 1977) of the entire 30 kDa coding region verified that the modified cDNA encoded the correct amino acid sequence for the human calpain protein (Ohno et al., *Nucl. Acids Res.* 14:5559, 1986).

This plasmid was then digested with BamHI and the 820-base-pair fragment containing the entire human 30 kDa calpain cDNA with its modifications for baculovirus expression: 1) addition of CCTATAAAT immediately 5' to the start codon to potentially improve transcription; and 2) changing the stop codon to the baculovirus-preferred TAA (Luckow et al., *Virology*, 170:31–39, 1989) was subcloned for single subunit expression into BamHI-digested pVL941 transfer vector containing the polyhedrin promoter. The resultant plasmid was designated pVL941-hCANP30-6. For two-subunit expression, the 820-bp fragment was subcloned into either BamHI- or BglII-digested pAcUW51 (PharMingen, San Diego, Calif.; designated p51-Bam-CANP30 and p51-Bgl-CANP30, respectively), a transfer vector containing both the p10 and polyhedrin promoters (see FIG. 3). The pAcUAW-51 vector is designed to express two proteins simultaneously from the same virus, inserting both into the polyhedrin locus of baculovirus. This vector contains two promoters—polyhedrin and p10—which are strong promoters that begin transcription very late in infection (i.e., after 18–24 hours). The promoters are inserted in the vector in opposite orientation to minimize deletion of the cDNAs by homologous recombination due to duplication of the genetic material (Weyer et al., *J. Gen. Virol.*, 70: 203–208 (1991). Resulting plasmids were verified as having only one insert in the correct orientation for expression by restriction enzyme analysis (data not shown).

EXAMPLE 2

Cloning the Human Calpain 80 kDa Subunit

Figure 2:
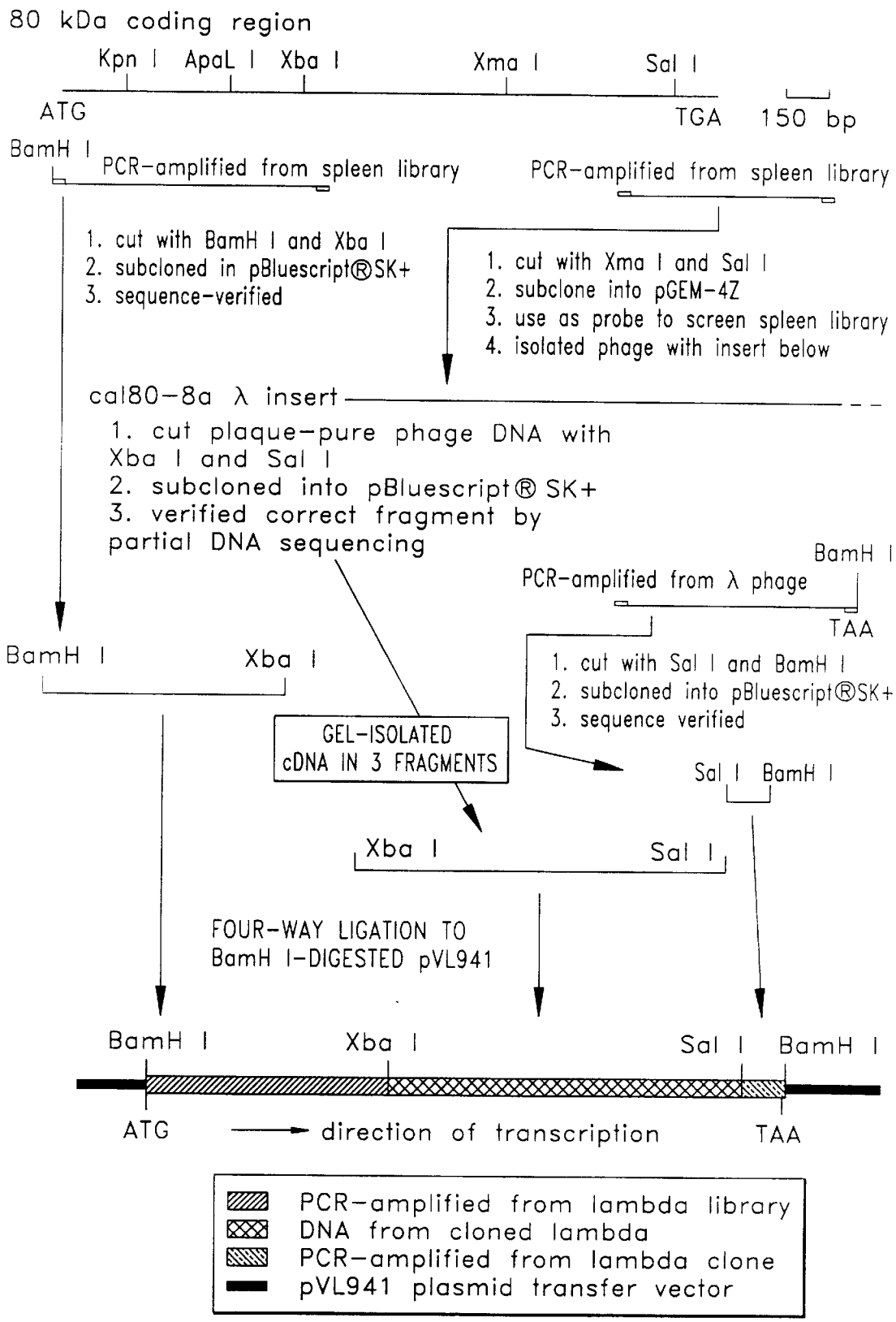
FIG. 2 depicts the cloning strategy for the 80 kDa calpain I subunit.

FIG. 2 depicts the strategy for cloning the human 80 kDa calpain I subunit. Primers SM-40 5'>GTACACT-TGAAGCGTGACTTC>3' and SM-41 5'>CAGGCAG-CAAACGAAATTGTC>3' were prepared and used to amplify base pairs #1372–2037 of the human 80 kDa cDNA from the HL1134a human spleen λgt10 library (Clontech Laboratories, Inc., Palo Alto, Calif.) for use as a probe. Conditions for the PCR were as above for Taq DNA polymerase with the solution being made 2 mM with respect to MgSO$_4$ and the addition of 5 µl of lambda library using 30 amplification cycles of 1 minute at 94° C., 1 minute at 60° C. and 2 minutes at 72° C. The PCR-amplified fragment was isolated away from primers following the supplied instructions with the Wizard PCR prep kit (Promega, Madison, Wis.). This fragment was digested with XmaI and SalI. The resulting 538 bp fragment was isolated from a 1% Seakem-GTG/2% NuSieve (FMC BioProducts, Rockland, Me.) agarose gel using the supplied protocol for the GeneClean II kit (B101, La Jolla, Calif.) and then ligated to XmaI-, SalI-digested pGEM-4Z vector (Promega, Madison, Wis.).

DNA from the above partial cDNA clone of the 80 kDa subunit was digested with EcoRI and HindIII to release the insert, followed by isolation of the fragment using the GeneClean II kit after electrophoresis in a 1% Seakem-GTG/2% NuSieve agarose gel. It was then labeled with [32]P-dCTP and used to screen the human spleen library as described above. Approximately 500,000 plaque forming units were plated on a ten, 150 mm diameter, petri plates. Duplicate nitrocellulose lifts were prepared and hybridized with the denatured labeled probe overnight at 68° C. in the same hybridization mix as described above for the 30 kDa screen, followed by two washes with 2×SSC, 0.1% SDS for 15 minutes each at room temperature and two washes with 1×SSC, 0.1% SDS for 1 hr each at 68° C., with detection of the labeled plaques by autoradiography.

One phage (lambda cal80-8a) was found to have an insert containing 67% of the 3' end of the coding region of the cDNA for the 80 kDa subunit. DNA was isolated from a liquid culture of plaque-purified phage following methods described in Sambrook et al., supra, digested with XbaI and SalI, and the unique 1238 bp 80 kDa cDNA fragment was isolated from a 1% SeaKem-GTG agarose gel using the supplied protocol for the GeneClean II kit (B101, La Jolla, Calif.). This fragment was ligated to XbaI-, SalI-digested pBluescript® SK+vector (Stratagene, La Jolla, Calif.) and the identity of the insert verified by dideoxynucleotide DNA sequencing (Sanger et al., supra) of portions of the insert.

The other sections of the coding region of the cDNA were generated by PCR amplification either from the human spleen library (5' end) or the plaque-purified lambda phage cal80-8a (3' end). Amplification of the 3' end was done to remove 3' untranslated sequences and change the stop codon to the baculovirus-preferred TAA. For the former, primers SM-53 5'>CGCGGATCCTATAAATATGTCGGAG-GAGATCATCACGCCG>3' and SM-49 5'>ATTTGCG-GATGGTCCGGCTCTTGA>3' were used to amplify base pairs #1–1096 of the human 80 kDa cDNA from 10 ml of the HL1134a human spleen library. Primer SM-53 adds a BamHI site to facilitate subsequent cloning and inserts the sequence CCTATAAAT immediately before the start codon in an attempt to achieve optimal baculovirus translation. For the latter, primers SM-40 5'>GTACACTTGAAGCGT-GACTTC>3' and SM-47 5'>CGGGATCCTTATGCAAA-CATGGTCAGCTGCAACC>3' were used to amplify base pairs #1372–2143 of the human 80 kDa cDNA from 1 µl of lambda phage cal80-8a. Amplifications were carried out with UlTma DNA polymerase (Perkin-Elmer, Norwalk, Conn.) using the supplied buffer with the addition of 40 µM dNTP's and 1.5 mM added MgCl$_2$. The amplification cycles were as follows: 5 minutes denaturation step at 95° C. before addition of the polymerase, followed by 30 amplification cycles of 1 minute at 94° C., 1 minute at 60° C., and 2 minutes at 72° C.

The 1096 bp fragment with the 5' end was isolated using the GeneClean II kit after electrophoresis in a 1% Seakem-GTG/2% NuSieve agarose gel. This fragment was then digested with BamHI and XbaI, repurified after digestion using the GeneClean II kit and subcloned into BamHI-, XbaI-digested pBluescript® SK+vector (Stratagene, La Jolla, Calif.). The 3' end PCR-amplified fragment was isolated away from primers following the supplied instructions with the Wizard PCR prep kit (Promega, Madison, Wis.). This fragment was then digested with SalI and BamHI, the resultant 137 bp fragment isolated from a 1% Seakem-GTG/2% NuSieve (FMC BioProducts, Rockland, Me.) agarose gel using the supplied protocol for the Mermaid kit (B101, La Jolla, Calif.) and then ligated to SalI-, BamHI-digested pBluescript® SK+vector (Stratagene, La Jolla, Calif.). Dideoxynucleotide DNA sequencing (Sanger et al., supra) of both of these inserts verified that they encoded the correct amino acid sequence (Aoki et al., *FEBS Lett.* 205: 313–317, 1986) for that portion of the protein and was used to eliminate clones with mutations from the polymerase chain reaction amplification.

The BamHI, XbaI fragment with the modified 5' end of the coding region, the XbaI, SalI fragment with the middle of the coding region, and the SalI, BamHI fragment from the 3' end of the coding region were digested with the appropriate enzymes from their vectors and the fragments isolated from a 1% Seakem-GTG/2% NuSieve (FMC BioProducts, Rockland, Me.) agarose gel using the supplied protocol for the GeneClean II kit (B101, La Jolla, Calif.). These fragments were then mixed in equimolar amounts with pVL941 vector (Luckow and Summers, *Virology* 170:31–39, 1989) that had been digested with BamHI and treated with shrimp alkaline phosphatase (U.S. Biochemical Corp., Cleveland, Ohio) following the manufacturer's protocol and ligated together. A clone (plasmid designation pVL941-hCANPI80-4) containing the correctly-sized BamHI fragment in the proper orientation, as determined by restriction enzyme analysis, was used for the production of the recombinant baculovirus expressing only the 80 kDa subunit (see below).

Figure 3:
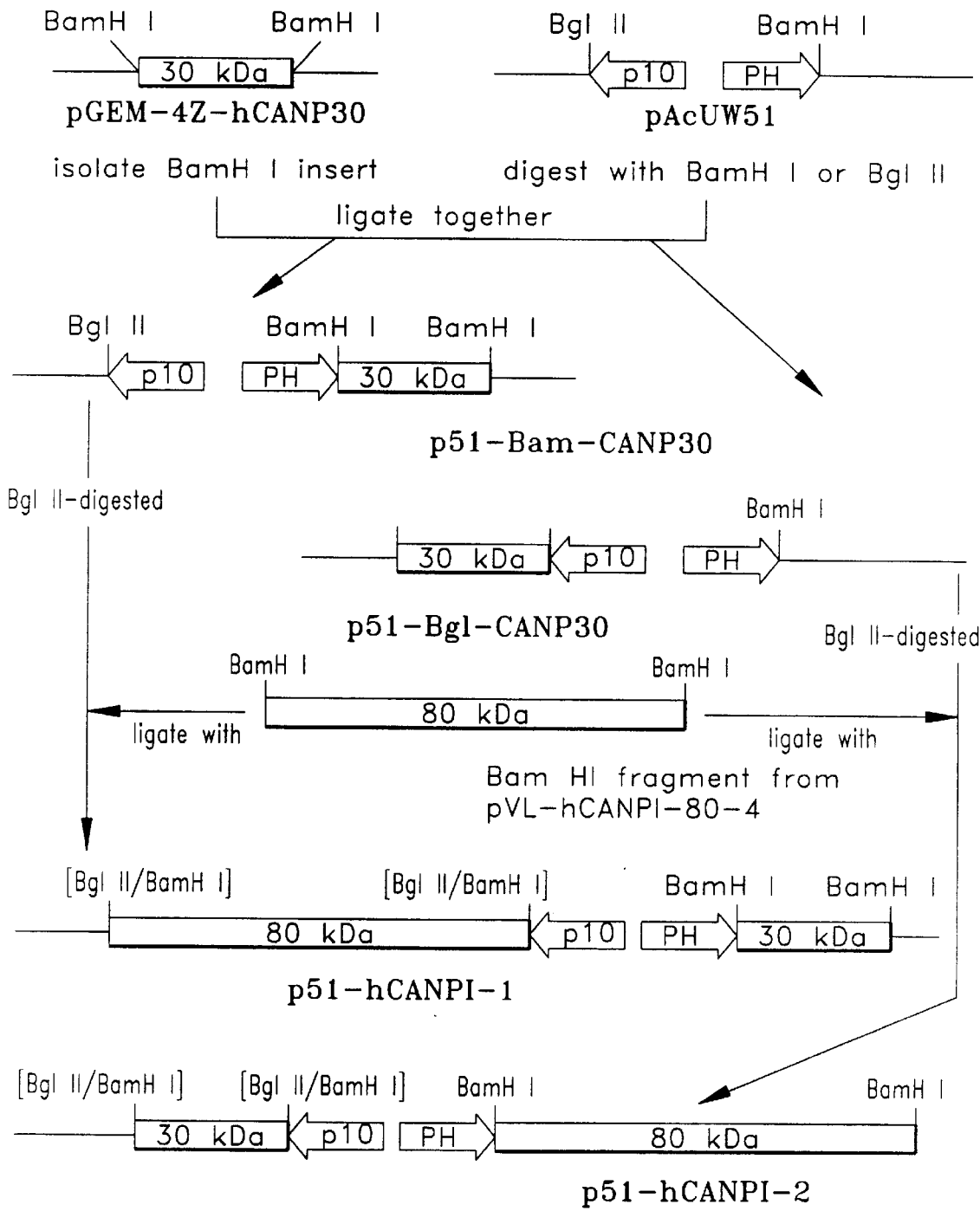
FIG. 3 depicts the cloning strategy for the double construct.
Figure 5A:
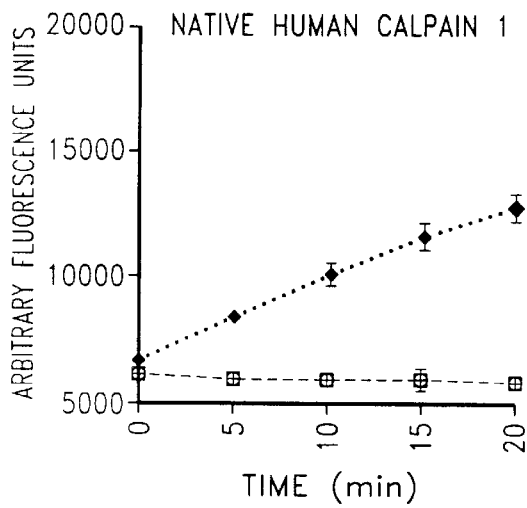
FIGS. 5 a–d depict measurement of calcium-dependent protease activity.
Figure 5B:
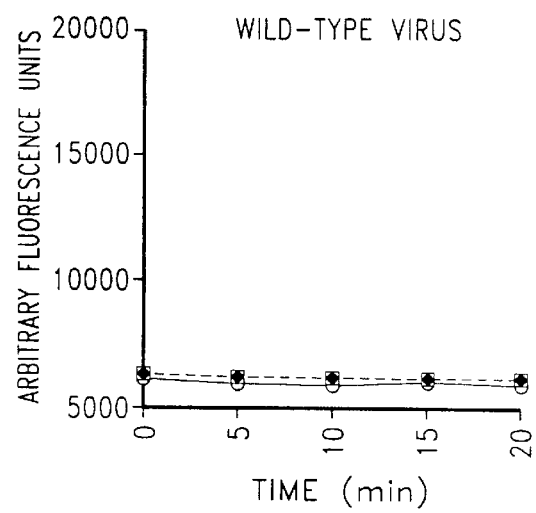
Figure 5C:
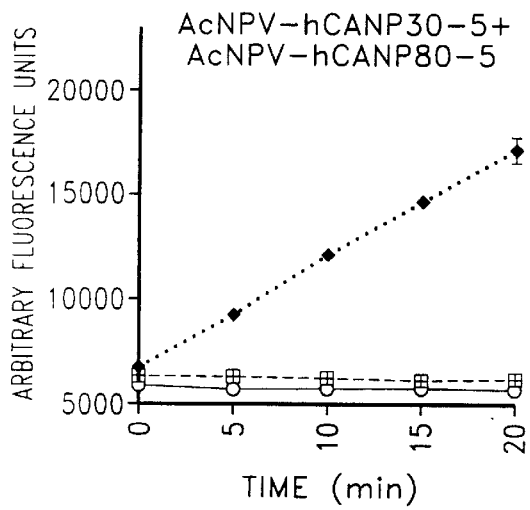
Figure 5D:
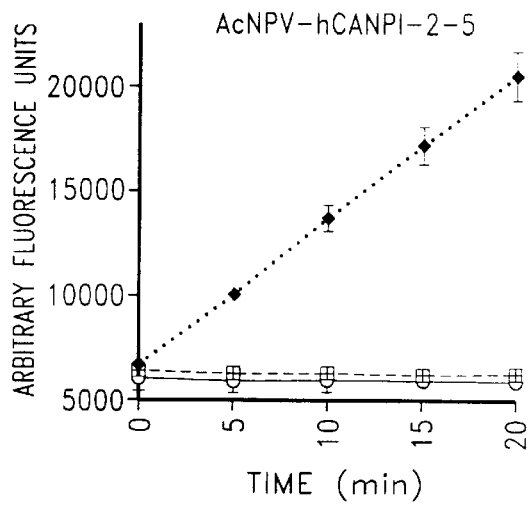

Plasmid PVL941-hCANI80-4 was also digested with BamHI and the 2153 bp fragment containing the entire human 80 kDa calpain I cDNA was subcloned into either BamHI-digested p51-Bgl-CANP30 or BglII-digested p51-Bam-CANP30 for the production of single vectors containing cDNAs for both subunits, i.e. double constructs (see FIG. 3). The resulting plasmids (designated p51-hCANPI-1 and p51-hCANPI-2, respectively) were verified as having only one new insert in the correct orientation for expression by restriction enzyme analysis.

The above represents the method that was used to clone the cDNAs for human calpain I. There are a number of comparable methods known to those skilled in the art that could allow one to obtain cDNA sequences of these genes suitable for recombinant expression. Similar methods could also be used to obtain the cDNA for calpain II for recombinant expression.

The same strategy was used to generate a probe for library screening to obtain the human calpain II 80 kDa cDNA. The cDNA for the coding region of the 80 kDa subunit of calpain II is reported in Imajoh et al., supra (incorporated herein by reference). Primers SM-69 5'>CATTGATGATGGAGT-CAGGAG>3' and SM-70 5'>CTGAGAAACAGAGCCAA-GAGA>3' were used to amplify bp #1587–2075 from the same human spleen library. Conditions for the PCR are described above using 2 units of Tli DNA polymerase (Promega, Madison, Wis.) with 0.75 Mm added $MgCl_2$ and 10 µl of lambda library using 30 amplification cycles of 1 minute at 94° C., 1 minute at 55° C. and 1 minute at 72° C. The 489 bp fragment was isolated from a 1% Seakem-GTG/2% NuSieve (FMC BioProducts, Rockland, Me.) agarose gel using the supplied protocol for the GeneClean II kit (Bio101, LaJolla, Calif.), digested with PstI and BamHI, and the procedure just described used to isolate the 377-bp PstI-, BazEI-fragment after agarose gel electrophoresis. The purified fragment was ligated to PstI-, BamHI-digested pGEM-4Z vector (Promega, Madison, Wis.).

EXAMPLE 3

Production of Recombinant Baculoviruses

*Spodoptera frugiperda* cells (Sf21; Vaughn et al., *In Vitro*, 13:213–217, 1977) were provided by Dr. B. G. Corsaro of the Boyce Thompson Institute for Plant Research, Cornell University, Ithaca, N.Y. These cells were grown in suspension at 27° C. in supplemented Grace's medium (JRH Biosciences, Lenexa, Kans.) with the addition of 10% defined fetal bovine serum (Hyclone Laboratories, Inc., Logan, Utah). Monolayer cultures for some expression studies and plaque assays were obtained by seeding the suspension-grown cells in tissue culture flasks at the densities indicated for the applications.

Recombinant baculoviruses were produced by cotransfecting Sf21 cells in a monolayer culture (approximately $2 \times 10^6$ cells in a 25 $cm^2$ flask) with 0.5 mg of linearized AcNPV DNA (Baculogold®, PharMingen, San Diego, Calif.) and 2 mg of one of the four vectors described above (listed below in Table II) using Insectin® liposomes following the supplied protocol from InVitrogen (San Diego, Calif.). The resulting culture supernatant containing primarily recombinant baculoviruses was harvested 2–5 days later and used to set up plaque plates of the extracellular virus.

TABLE II

| Vector | Calpain subunit | Promoter |
| --- | --- | --- |
| pVL941-hCANP30-6 | 30 kDa | polyhedron |
| pVL941-hCANPI80-4 | 80 kDa | polyhedron |
| p51-hCANPI-1 | 30 kDa | polyhedron |
|  | 80 kDa | p10 |
| p51-hCANPI-2 | 30 kDa | p10 |
|  | 80 kDa | polyhedron |

Sf21 cells were seeded in 60-mm culture dishes ($2 \times 10^6$ cells/dish) and infected for one hour with 1 ml of 10-fold serial dilutions of the cotransfection culture supernatant ($10^{-2}$ to $10^{-5}$) and subsequently overlaid with 4 ml of a 1:1 mixture of 2× supplemented Grace's medium (Gibco BRL, Gaithersburg, Md.) and 2% Seakem agarose (FMC Bioproducts, Rockland, Me.). Putative recombinant plaques were identified 5–7 days later by visual inspection for occlusion-body-negative plaques using both a dissection and an inverted-phase microscope following 7 minutes staining with 0.05% neutral red in Dulbecco's PBS. Plaques were verified as being recombinant by the hybridization of [32] P-labeled 30 kDa or 80 kDa human calpain I sequences to blots of infected cell lysates (Summers and Smith, *A Manual of Methods for Baculovirus Vectors and Insect Cell Culture Procedures*, Texas Agricultural Experiment Station Bulletin 1555: 1–57, 1987). Recombinant virus was then expanded for the first two passages in monolayer Sf21 cultures, with subsequent virus passages (minimum of three to a maximum of five) using suspension Sf21 cultures. All virus expansions were carried out by infecting Sf21 cells at a multiplicity of infection (MOI) of less than 0.5 and collecting the medium containing the extracellular virus particles 3–4 days after infection.

Seven independent plaque-pure recombinant viruses (recombinant viruses designated AcNPV-hCANP30-1 through -7, respectively) were isolated from the transfection of cells with pVL-hCANP30-6. AcNPV-hCANP30-5 was deposited Jun. 2, 1994, with the American Type Culture Collection, 12301 Parklawn Drive, Rockville, Md. 20852-1776 (hereinafter "ATCC") and bears ATCC designation ATCC VR 2459. Six independent plaque-pure recombinant viruses (recombinant viruses designated AcNPV-hCANPI80-1 through -6, respectively) were isolated from the transfection of cells with pVL-hCANPI80-4, all of which contained the DNA for the 80 kDA subunit only. AcNPV-hCANPI80-5 was deposited on Jun. 2, 1994, with the ATCC and bears ATCC designation ATCC VR 2457. Twelve independent plaque-pure recombinant viruses (designated AcNPV-hCANPI-1-2, 1-5, 1-7 and 1-8 and AcNPV-hCANPI-2-1 through 2-8, respectively), were isolated from the cotransfections of cells with p51-hCANPI-1 and p51-hCANPI-2. Of the 12 recombinant viruses isolated, only 5 contained the DNA for both the 30 kDa and 80 kDa subunits. These 5 recombinant viruses were AcNPV-hCANPI-1-5, ACNPV-hCANPI-1-7, AcNPV-hCANPI-1-8, AcNPV-hCANPI-2-3, and AcNPV-hCANPI-2-5. AcNPV-hCANPI-2-5 was deposited on Jun. 2, 1994, with the ATCC and bears ATCC designation ATCC VR 2458. The eighteen selected recombinant viruses obtained were then examined for their ability to express the calpain protein as described below. All deposits were made under the provisions of the Budapest Treaty for the International Recognition of the Deposit of Microorganisms for the Purpose of Patent Procedure, all aspects of which are herein incorporated by reference. All deposits were tested by the ATCC and determined to be viable at the time of deposit.

EXAMPLE 4

Expression and Recovery of Baculovirus Recombinant Calpain

Sf21 cells were seeded in 24 well plates at $1.5 \times 10^5$ cells/cm$^2$ in supplemented Grace's medium with 10% fetal bovine serum. After cell attachment, virus (see below for specific virus designations) was added at an MOI of between 1 and 5. The cells were harvested sometime after 24 hours. With the present expression system, optimal yield was achieved with harvests between 36–48 hours after infection. For the harvest, a lysis buffer of 50 mM Tris-HCl, 10 mM EDTA, 0.1 mM phenylmethylsulfonyl fluoride (PMSF), 1 μg/ml leupeptin, and 0.1% NP-40, pH 7.4 was used, followed by centrifuging the homogenates in an Eppendorf tube at 14,000×g for 10 minutes at 4° C. and recovering calpain and other cellular proteins. Proteins were denatured by adding 0.2% SDS and heating the samples for 5 minutes at 95° C. Samples were then stored at −70° C. prior to analysis.

The calpain expressed and recovered was examined by immunoblot analysis as follows. Ten to twenty micrograms of total protein was separated by SDS-PAGE (Laemmli, 1970) using 10% or 12.5% acrylamide gels and transferred to 0.45 mm nitrocellulose (Bio-Rad, Melville, N.Y.) by the method of Towbin et al., *Proc. Natl. Acad. Sci. USA* 76: 4350–4354 (1979). Calpain protein was specifically detected using a 1:1,000 dilution of polyclonal anti-calpain serum which detects both subunits (Siman et al., *J. Neurosci.* 10:2400–2411, 1990). The antiserum was diluted in 20 mM Tris-HCl, pH 7.4, with 150 mM NaCl and 5% Carnation nonfat dry milk (blocking buffer). Non-specific antibody binding was removed by washing with 20 mM Tris-HCl, pH 7.4, with 150 mM NaCl and 0.05% Tween-20. Alkaline-phosphatase-conjugated goat anti-rabbit IgG (Bio-Rad, Melville, N.Y.), diluted 1:2,000 in blocking buffer, was then added. The secondary antibody was detected using the alkaline phosphatase conjugate substrate kit (Bio-Rad, Melville, N.Y.). The results for recombinant viruses AcNPV-hCANP30-5, AcNPV-hCANPI80-5, and AcNPV-hCANPI-2-5 are shown in FIG. 4.

The expression of the appropriate individual calpain subunit resulting from cells infected with the AcNPV-hCANP30-5 and AcNPV-hCANPI80-5 viruses alone are depicted in lanes 2–3 and 4–5, respectively. When the cells were coinfected with two viruses, one containing the DNA construct for the 30 kDa calpain subunit (AcNPV-hCANP30-5) and the other containing the DNA construct for the 80 kDa calpain subunit (ACNPV-hCANPI80-5), both appropriate calpain subunits were expressed. This is depicted in lanes 6–8. Similarly, when cells were infected with AcNPV-hCANPI-2-5, which contained the DNA construct for both the 30 kDa and 80 kDa calpain subunits, both ubunits were expressed (lanes 9–10). The ability of an anti-calpain serum to detect the recombinant protein verified that authentic calpain protein was produced. Lane 1 represents infection with wild-type virus. No calpain expression was detected.

Surprisingly, the accumulated amount of the 80 kDa ("catalytic") subunit was unexpectedly increased (as determined by visual inspection) by coexpression with the 30 kDa ("regulatory") subunit, either by coinfection of cells with AcNPV-hCANP30-5 and AcNPV-hCANP80-5 (lanes 6–8) or by expression of the double construct AcNPV-hCANPI-2-5 (lanes 9–10), as compared with expression in the absence of the 30 kDa subunit (lanes 4–5). Previous research into the role of the 30 kDa subunit would not allow one to predict this stabilizing effect on the other subunit.

Analysis of all of the AcNPV-hCANP30 and the AcNPV-hCANP80 recombinant viruses in the same fashion as above showed comparable levels of expression of their respective subunits (data not shown). While all five virus isolates of AcNPV-hCANPI containing both calpain subunits expressed the intact 80 kDa calpain subunit, four of the isolated viruses (i.e., AcNPV-hCANPI-1-5, AcNPV-hCANPI-1-7, AcNPV-hCANPI-1-8, and AcNPV-hCANPI-2-3) failed to also express detectable amounts of the 30 kDa calpain subunit (data not shown). The absence of the 30 kDa subunit was further evident by the decreased level of expression of the 80 kDa subunit, which was comparable to that seen with the AcNPV-hCANPI80 viruses, as opposed to the increased level observed with coinfections of AcNPV-hCANP30 and AcNPV-hCANPI80 and with infection with AcNPV-hCANPI-2-5. That only 5 out of 12 of the double subunit viruses still contained DNA sequences for both subunits following recombination and selection of recombinant viruses and that, of those 5, only one was found to coexpress both protein subunits, suggests the existence of a selection pressure against the insect cell expression of the complete two-subunit calpain protease. This might be a consequence of the lethality of calpain.

The additional bands visible around the 80 kDa subunit bands in FIG. 4 are a result of the autolytic enzyme activity. The two bands visible in lanes 6–8 represent the 80 kDa and autolytically-resultant 76 kDa forms, respectively. Two bands are also observed on the blot for lanes 9 and 10 but may not be visible in the Figure. Three bands are actually visible in lanes 4 and 5. In addition to the 80 kDa and autolytically-resultant 76 kDA forms, a stable intermediate of 77 kDa forms at low enzyme concentration and was previously reported to form upon autolysis of the large subunit in a calpain I heterodimer incubated with calcium under dilute conditions. (Inomata, et al., *J. Biol. Chem.*, 263:19783–19787, 1988.) As is apparent from FIG. 4, however, most of the recombinant human calpain recovered is in the 80 kDa form, which is desired in the instance of calpain considering the potential lethality to the system. Since calpain autolyses to the active form in the presence of calcium, no separate treatment is required for activation other than adding calcium.

EXAMPLE 5

Enzyme Activity of the Baculovirus Recombinant Calpain

Sf21 cells were again seeded in 24 well plates at $1.5 \times 10^5$ cells/cm$^2$ and infected with either wild-type virus, coinfected with both AcNPV-hCANP30-5 and AcNPV-hCANPI80-5 (MOI of 5 for each virus), or infected with AcNPV-hCANPI-2-5 (MOI=5.7). The intracellular proteins were harvested at 40 hours after infection with 100 μl/well of the following lysis buffer: 50 mM Tris-HCl, pH 7.5, 50 mM NaCl, 1 mM EDTA, 1 mM EGTA, 5 mM β-mercaptoethanol, 0.1% Triton-100, followed by a 10 minutes centrifugation at 14,000×g at 4° C. to pellet the nuclei and some membranes. The in vitro enzyme activity of 20 μl of each extract (12.5–20 μg of total protein) was measured using the synthetic peptide substrate succinyl-leucine-tyrosine-aminomethyl coumarin (Succ-Leu-Tyr-AMC) at a 1 mM concentration with and without the addition of 5 mM $CaCl_2$ following the procedure of Sasaki et al., *J. Biol. Chem.*, 259:12489–12494 (1984), incorporated herein by reference. The activity obtained was compared with the enzyme activity of 2 μg of partially-purified native human calpain I produced according to the method of Siman et al., supra.

The activity in the presence of calcium was also measured with the addition of 12.5 μM calpain inhibitor I following the procedure disclosed in Sasaki et al., supra. The results are depicted in FIGS. 5a–d. In FIGS. 5a–d, open circles represent activity without calcium present. Solid diamonds represent activity with calcium present. Crossed-squares represent activity with calcium and calpain inhibitor I present. The data in FIGS. 5a–d show 1) a calcium-dependent increase in substrate hydrolysis by native human calpain I that is inhibited by calpain inhibitor I (5a); 2) no endogenous calcium-dependent substrate hydrolysis in cells infected with wild-type virus (5b); and 3) in cells either coinfected with AcNPV-hCANP30 and AcNPV-hCANP80 (5c) or infected with AcNPV-hCANPI-2-5 alone (5d), there is a calcium-dependent increase in substrate hydrolysis that is also inhibited by calpain inhibitor I, just as seen with the native enzyme. Based on these results, the recombinantly produced calpain has the same enzyme activity profile as native calpain. Again, this is important for effective utilization of the recombinant enzymatically active calpain to screen potential calpain inhibitor therapeutics.

EXAMPLE 6

Autolytic Enzyme Activity of the Baculovirus Recombinant Calpain

The autolytic enzyme activity of the recombinant calpain was demonstrated by showing that the recombinant calpain correctly autoprocessed the 80 kDa subunit to the "activated" 76 kDa form. The 76 kDa form is produced in the presence of calcium by autolytic cleavage and is indicative of active enzyme. Lysates from cells either infected with wild-type AcNPV, coinfected with both AcNPV-hCANP30-5 and AcNPV-hCANPI80-5 or infected with AcNPV-hCANPI-2-5 prepared in Example 5 were incubated with or without the addition of 6.7 mM $CaCl_2$ for 5 minutes at room temperature, stopping the reaction by adding 6.7 mM EDTA and boiling the samples in SDS-PAGE-gel-loading buffer prior to storage at −70° C. The results of PAGE of the preparations are depicted in FIGS. 6a and b. In FIGS. 6a and b, the presence and absence of calcium is indicated by a "+" or "−", respectively. FIG. 6a depicts an anti-calpain I immunoblot with and without in vitro calcium incubation. The AB#4 antiserum preparation used was raised against purified native calpain. It primarily detects the 80 kDa subunit, although it will also bind the 76 kDa autolytic cleavage product. Lanes 1 and 2 contain the partially purified native human calpain I 80 kDa subunit (purified from human red blood cells as described previously, see Kitahara, et al., supra). Lane 3 contains the protein fraction from cells infected with the wild-type virus. Lanes 4 and 5 represent the protein fraction from cells cotransfected with AcNPV-hCANP30-5 and AcNV-hCANPI80-5. Lanes 6–7 represent the protein fraction from cells transfected with AcNPV-hCANPI-2-5. In the absence of added calcium, lanes 4 and 6 have two immunoreactive bands. Lane 1 (the native human calpain I purified from human red blood cells) has only one band. The upper bands of lanes 4 and 6 comigrate with the 80 kDa subunit of the native partially-purified human erythrocyte calpain I and the lower bands comigrate with the 76 kDa native human calpain I that has been incubated with calcium (lane 2). The lower bands, present even in the absence of calcium, appear to be endogenously activated calpain, presumably due to the intracellular influx of calcium from the medium as some cells become leaky during the infection. A single band is detected in all the samples incubated with calcium (lanes 2,5, and 7), and it comigrates with the 76 kDa native human calpain I (lane 2) that has also been incubated with calcium.

The data in FIG. 6b show that the protein migrating as a 76 kDa band is the properly-cleaved authentic 76 kDa autocatalytic fragment. FIG. 6b contains the results of an immunoblot analysis of the same samples as in 6a except that the AB#34 antibody used was generated against the first five amino acids at the N-terminus of the 76 kDa fragment (anti-LGRHEC); (Saido et al., *J. Biochem.* 111:81–96 (1992)). This antibody specifically recognizes only the properly-cleaved native human enzyme (i.e., 76 kDA; lane 2) and not the intact 80 kDa calpain I (lane 1). Both the small amounts of the endogenously-cleaved recombinant calpain I large subunit and the single abundant 76 kDa band after the addition of calcium are detected by this antiserum. The foregoing results demonstrate that the entire amount of the 80 kDa subunit recombinant protein is capable of being autocatalytically activated by the addition of calcium and that the activated subunit is properly cleaved.

EXAMPLE 7

Improved Expression in Serum-Free Medium

Spinner cultures of insect cells are routinely used for the baculovirus expression of recombinant proteins because of the greater ease in handling large numbers of cells as compared to monolayer cultures. A comparison was made between the production of calpain in Sf21 cells grown in supplemented Grace's medium with 10% defined fetal bovine serum versus Sf21 cells adapted to serum-free medium by serial two-fold dilutions to growth in ExCell-401 (JRH Biosciences, Lenexa, Kans.). Log-phase Sf21 cells grown in either medium were centrifuged at 150×g for 10 minutes to pellet the cells and resuspended at $10^7$ cells per ml in their growth medium containing AcNPV-hCANPI-2-5 virus at an MOI=2. Cells plus virus were incubated at room temperature for 1 hour with an occasional gentle resuspension of the cells by hand. The entire mixture was added to the appropriate medium in 250 ml spinner flasks (Techne, Inc., Princeton, N.J.) to achieve a final volume of 100 ml at a cell density of $1.5 \times 10^6$ cells per ml. Duplicate infections for each medium were incubated at 27° C. with stirring, at a speed of 80 rpm for the serum-containing cultures and at 100 rpm for the serum-free cultures. Cultures were sampled at 24 hours and 48 hours.

Figure 7:
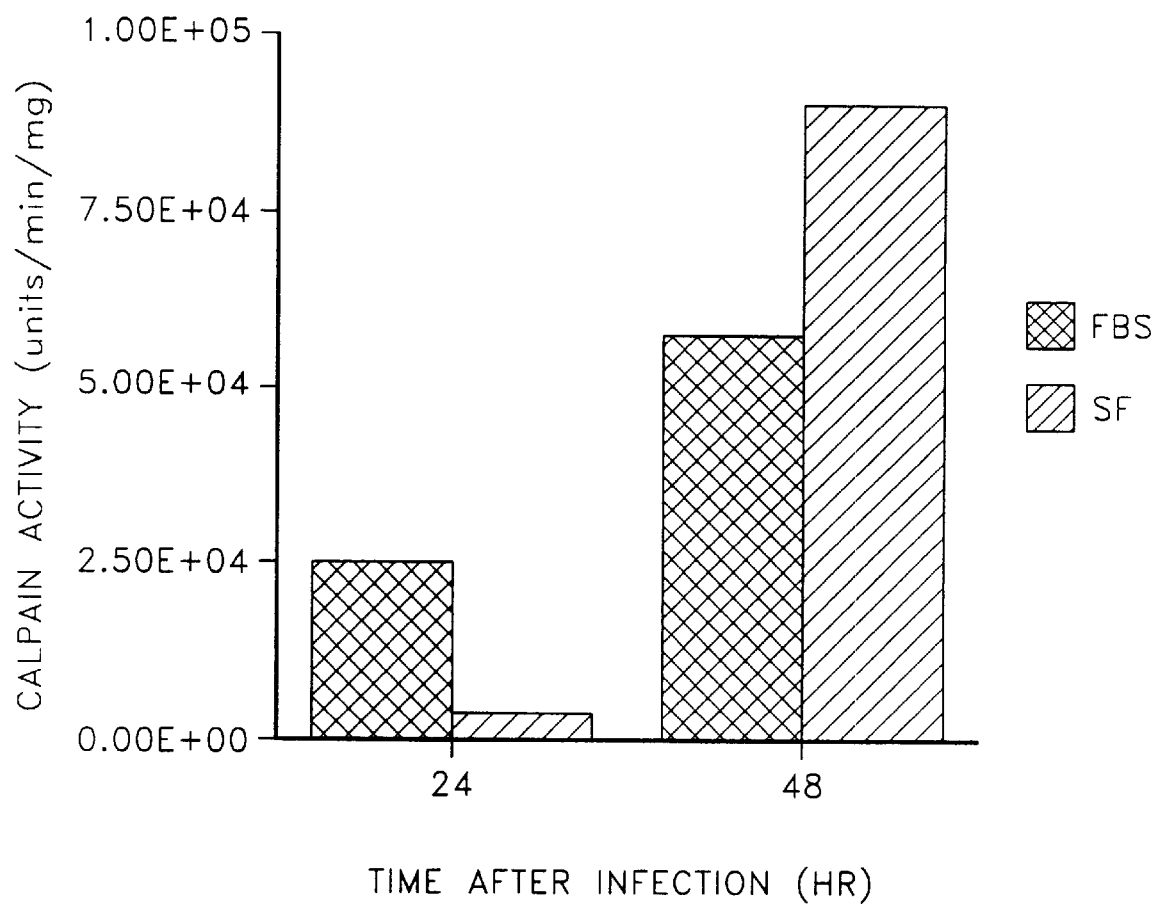
FIG. 7 depicts improved expression in serum-free medium.

Samples were harvested to permit measurement of the enzyme activity as described in Example 5, following pelleting of the cells by centrifuging at 150×g for 10 minutes, resuspension in Dulbecco's phosphate-buffered saline (Mediatech, Inc., Herndon, Va.), and then again centrifuging at 150×g for 10 minutes. Total protein concentrations were measured using the Bio-Rad protein assay (Bio-Rad Laboratories, Inc., Melville N.Y.) following the supplied protocol, with bovine serum albumin as the reference protein standard. The serum-free-adapted cells had unexpectedly low levels of recombinant calpain protein and activity at 24 hours, but unexpectedly higher levels than the serum cultures at 48 hours (FIG. 7). More importantly, there was proportionately less of the activated 76 kDa protein at 48 hours in the serum-free cultures as compared to the serum-containing cultures (data not shown). The higher amount of activated calpain at 48 hours in the serum-containing cultures made it impossible to purify intact, inactivated calpain at that time point (data not shown); accordingly, the use of the serum-free medium for the expression allowed a 3-4-fold increase in the starting concentration of recombinant calpain for purification compared with the level at 24 hours in serum-containing cultures.

EXAMPLE 8

Enzymatic Activity of Independent 80 kDa Subunit

Figure 8:
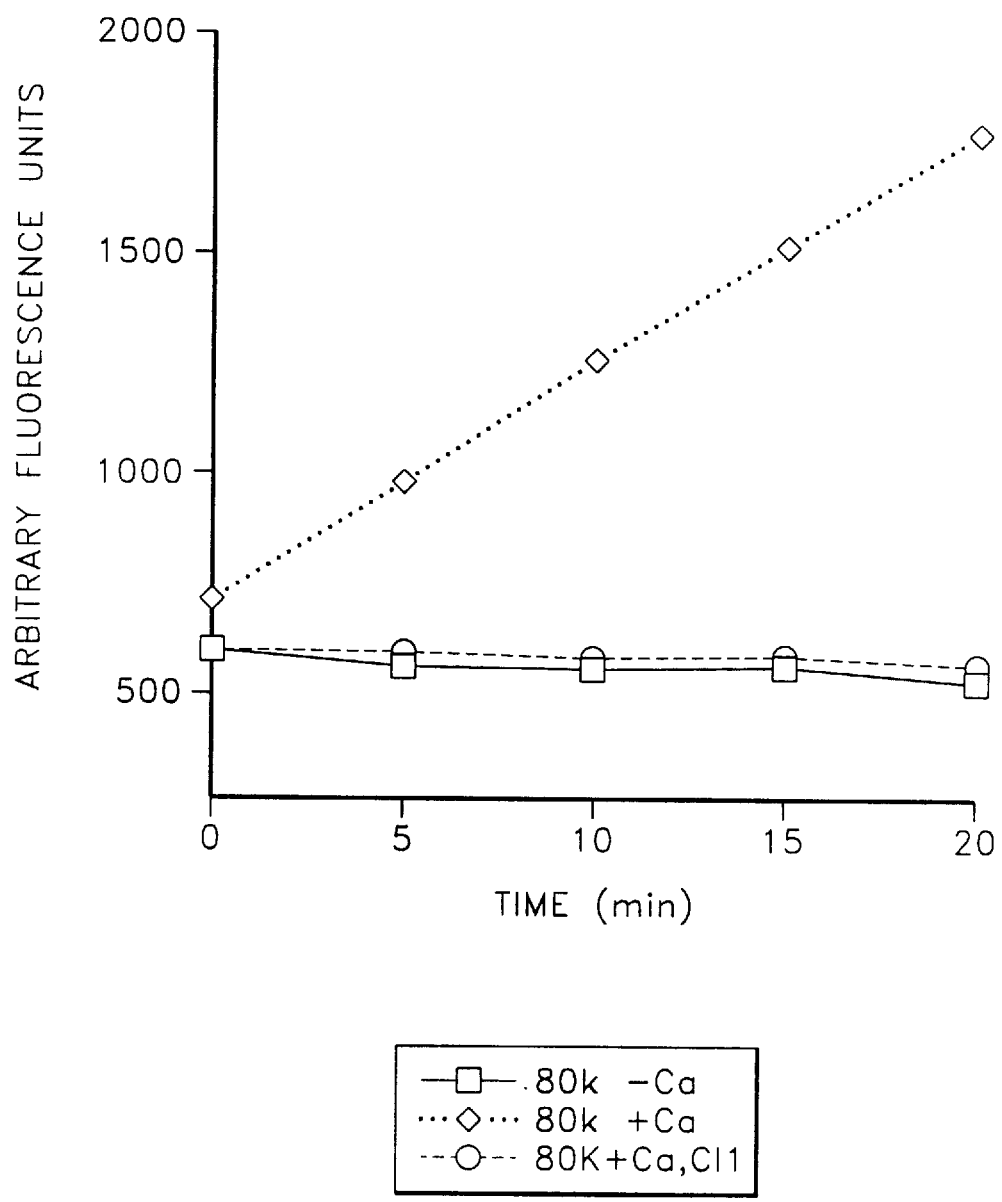
FIG. 8 depicts measurement of calcium-dependent protease activity of the 80 kDA subunit expressed alone.

To determine the relative activity of the recombinantly produced 80 kDa subunit, the enzymatic activity of the subunit was examined in unfractionated extracts from Sf21 cells infected with AcNPV-hCANPI80-5. $1.5 \times 10^8$ Sf21 cells were pelleted by centrifugation at 150×g, the medium removed, then resuspended with $3 \times 10^8$ pfu of AcNPV-hCANPI80-5 virus in 10 ml of supplemented Grace's medium with fetal bovine serum and incubated for 1 hr at 27° C. Following the incubation, the cells plus medium plus virus were added to 90 ml of the same medium and incubated at 27° C. in a 250 ml spinner flask for 24 hours. Cells were harvested as in Example 5 and the extract was examined for enzymatic activity also as described in Example 5. The results from 33 $\mu$g of unfractionated extract are depicted in FIG. 8. In FIG. 8, open squares represent activity without calcium present. Open diamonds represent activity with calcium present. Open circles represent activity with calcium and calpain inhibitor I present. The same amount of enzyme activity for both the recombinant 80 kDa subunit and the recombinant calpain was then run on SDS-PAGE and the amount of each was qualitatively determined by immunoblot analysis as described in Example 4 above. As determined therefrom, approximately 4- to 5-fold more isolated 80 kDa protein is needed to give activity equivalent to that of the heterodimeric protein. Thus, the specific activity of the 80 kDa recombinant calpain I was experimentally determined to be approximately 20–25% that of the heterodimeric calpain I. This is approximately seven times greater than that of the 80 kDa subunit dissociated from native calpain I (Kikuchi et al., supra). The activity was also shown to be completely inhibited by 12.5 $\mu$M calpain inhibitor I, as is the heterodimer enzyme (FIG. 8).

EXAMPLE 9

Purification of Recombinant Enzymatically Active Calpain

As disclosed below, recombinant calpain was purified in four steps, including three chromatographic steps, to 94% purity as determined by reversed-phase HPLC analysis. Cell culture conditions were as described in Example 7. The cells were lysed in a solution containing 10 mM HEPES, 2 mM EDTA, 2 mM EGTA, 5 mM β-mercaptoethanol, 5 mM pepstatin, 0.1 mM PMSF, and 10 mg/ml aprotinin, pH 7.5 and homogenized using a 40 ml Dounce homogenizer (Wheaton, Millville, N.J.). The material was then centrifuged at 2,100×g for 10 minutes to pellet nuclei, followed by centrifugation at 38,700×g for 1 hour to pellet membranes. The supernatant was precipitated with ammonium sulfate and proteins that precipitated between 30 to 451% ammonium sulfate were resuspended in a buffer solution containing 10 mM HEPES, 2 mM EDTA, 2 mM EGTA, 10 mM NaCl, and 5 mM β-mercaptoethanol, pH 7.5, dialyzed overnight against the same buffer, and then separated on the following resins using standard techniques: Q-Sepharose Fast Flow, followed by Phenyl Sepharose CL-4B (both from Pharmacia, Piscataway, N.J.), then Mimetic Red 2 (American International Chemical, Natick, Mass.). Following this technique, 5–6 mg of highly-purified protein was isolated from 1 liter of cells. A 15.5-fold purification was effected in three (3) chromatographic separations to yield a protein with a high degree of purity. Purification of calpain from human erythrocytes required over a 22,000-fold purification with four (4) chromatographic steps (Hatanaka et al., supra). This represents a major advantage of this recombinant expression in being able to easily purify larger quantities of calpain than can be easily done from native sources. For each analysis, enzyme activity was determined by monitoring the rate of hydrolysis in the presence of $Ca^{2+}$ of the synthetic fluorogenic substrate Succ-Leu-Tyr-methoxyl-β-naphthylamine (Succ-Leu-Tyr-MNA) similarly to the method used by Sasaki, T. et al., supra, for measuring hydrolysis of Succ-Leu-Tyr-AMC. The experiments were performed in 96 well plates (Dynatech cat# 011-010=7905, 14340 Sullyfield Circle, Chantilly, Va. 22021) and the fluorescence was detected using a 96 well plate reading fluorimeter (excitation=340 nM, emission=430 nM; Titertek Fluoroskan II Finland).

EXAMPLE 10

Comparative Sensitivities of Native and Recombinant Enzymatically Active Calpain to Inhibitors Native and recombinant enzymatically active calpain I were compared for their sensitivities to a number of known calpain I inhibitors. To evaluate inhibitor sensitivities, stocks (40 times concentrated) of each inhibitor to be tested were prepared in 100% anhydrous DMSO and 5 $\mu$l of each inhibitor preparation were aliquoted into each of three wells of a 96 well plate. Dilutions of each enzyme preparation were made into assay buffer (i.e., 50 mM Tris, 50 mM NaCl, 1 mM EDTA, 1 mM EGTA, and 5 mM β-mercaptoethanol, pH 7.5 including 0.2 mM Succ-Leu-Tyr-MNA) and 175 $\mu$l of each dilution aliquoted into the same wells containing the independent inhibitor stocks as well as to positive control wells containing 5 $\mu$l DMSO, but no inhibitor. To start the reaction, 20 $\mu$l of 50 mM $CaCl_2$ in assay buffer was added to all wells of the plate, excepting three, which were used as background signal baseline controls. Substrate hydrolysis was monitored every 5 minutes for a total of 30 minutes. Substrate hydrolysis in the absence of inhibitor was linear for up to 15 minutes. The rate of hydrolysis was determined as the change in fluorescence units per the 10 minute time period between 5 and 15 minutes. At each inhibitor concentration tested, the percent inhibition was determined as the percent decrease in the rate of substrate hydrolysis in the presence of inhibitor versus the rate in its absence. The 50% inhibition concentration ($IC_{50}$) determinations for three structurally diverse known inhibitors of calpain—Z-Leu-Phe-CONHEt, Z-Leu-Leu-Phe-$CH_2S(+)Me_2Br(-)$ and Z-Leu-Nle-H—are depicted in Table III below. Note that the IC$_{50}$s obtained for each calpain inhibitor against recombinant human calpain approximated those found for the native enzyme. The rank order of inhibitor potency was the same. Prototypic inhibitors of serine (PMSF) and aspartic proteases (pepstatin A) were also included in this determination. Both the recombinant and native enzymes showed insignificant inhibition of their activities by these class specific inhibitors as exemplified by the 5–6 fold order of magnitude greater differences in the IC$_{50}$ values obtained with respect to the known calpain inhibitors.

TABLE III

Inhibitor Profile

|  | Native | Recombinant |
| --- | --- | --- |
|  | (IC$_{50}$, nM) | |
| Z—Leu—Phe—CONHEt | 56 | 34 |
| Z—Leu—Leu—Phe—CH$_2$S(+)Me$_2$Br(−) | 14 | 8 |
| Z—Leu—Nle—H | 14 | 10 |
| Pepstatin A | >10,000 | >10,000 |
| PMSF | >1,000,000 | >1,000,000 |

EXAMPLE 11

Comparison of Calcium Activation of Native and Recombinant Calpain

Figure 9:
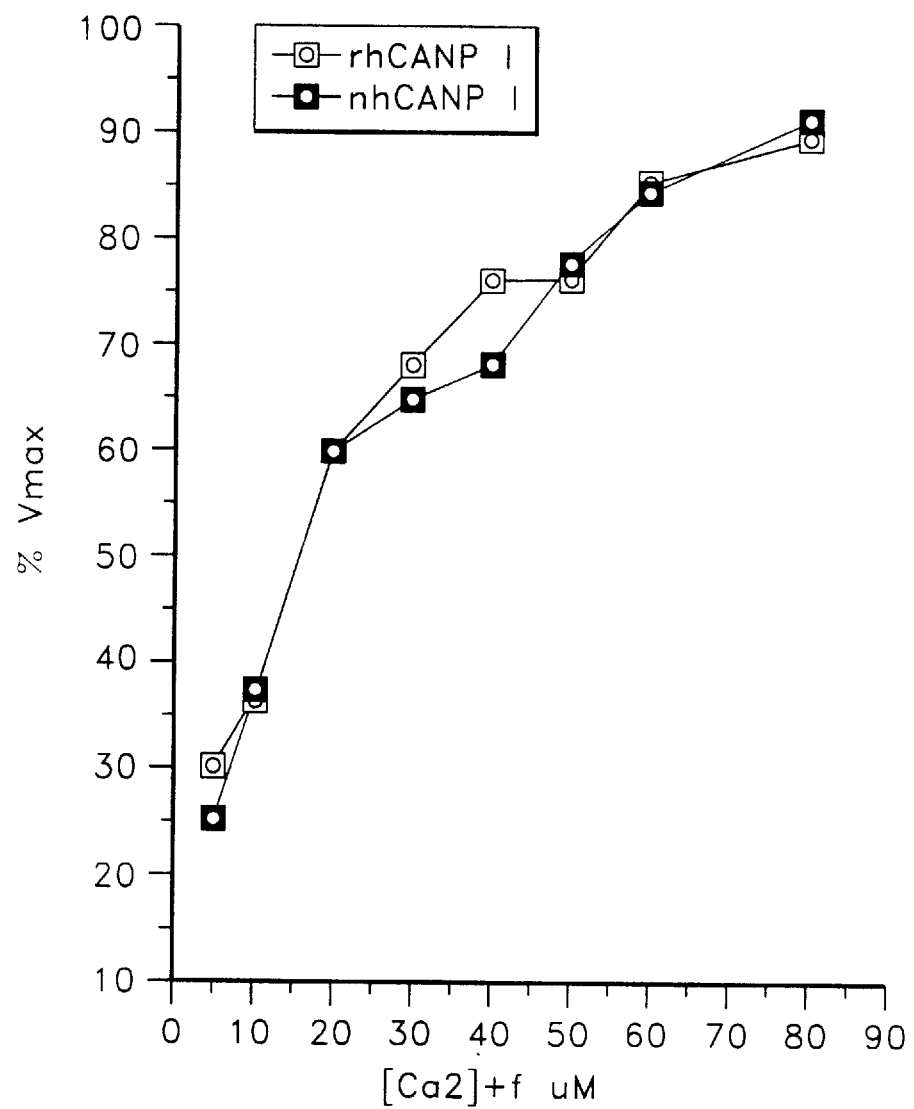
FIG. 9 depicts the calcium activation profiles of recombinant and native human calpain I.

To determine the calcium concentration required for enzyme activity, tests were performed essentially as described by Kitahara et al., *J. Biochem.*, 95:1759–1766 (1984). First, enzyme preparations were dialyzed overnight against 110 mM imidazole-HCl/1 mM EGTA buffer at pH 7.3 containing 5 mM β-mercaptoethanol. Ten-fold concentrated Ca$^{2+}$/EGTA buffers were prepared by adding varying amounts of CaCl$_2$ to the imidazole/EGTA buffer. Twenty μl of each buffer was put into three wells of a 96 well plate. Dilutions of dialyzed enzyme were made into the imidazole/EGTA buffer containing 1 mM Succ-Leu-Tyr-MNA and 180 μl of each preparation were added to the wells containing the various Ca/EGTA buffers. Substrate hydrolysis was measured every 5 minutes for 30 minutes. The ½ V$_{max}$ was determined as the rate of substrate hydrolysis which was 50% of the maximal rate achieved in the presence of the varying amounts of calcium. The results are shown in FIG. 9. The ½ V$_{max}$ listed is an approximation of the [Ca$^{2+}$] based on the K$_d$ of EGTA for calcium in this buffer at the particular ionic strength, pH, and temperature (K$_d$=5.5×10$^{-6}$M). The concentration of calcium required to give ½ V$_{max}$ was essentially the same for both native calpain and the recombinant calpain of this invention—i.e. 15 μM and 14 μM, respectively. The [Ca$^{2+}$] activation profiles for both the native and recombinant enzymes are virtually identical. In FIG. 9, open squares with interior open circles represent recombinant human calpain I (rhCANPI). Shaded squares with interior open circles represent native human calpain I (nhCANPI).

EXAMPLE 12

Assay for Calpain Inhibitors

Recombinant enzymatically active calpain is purified, for example, as described in Example 9 above. The purified calpain can then be utilized in an assay for screening potential inhibitors of calpain. The assay conditions can be similar to those described in Examples 9 and 10 above. For example, Succ-Leu-Tyr-MNA can be used as the substrate. Calpain inhibitor I can be used as a control for assaying inhibition of calpain. However, other substrates and known inhibitors can be utilized. (See Sasaki, supra.) Samples without calpain inhibitor I present can be used as enzyme activity controls. Each compound to be tested as a calpain inhibitor is assayed, for example, by the method described in Example 10 where known inhibitors were assayed. However, other methods can be utilized.

The disclosures of all of the patents and publications discussed or described herein are hereby incorporated by reference herein, in their entirety.

The foregoing examples are meant to illustrate the invention and not to limit it in any way. Those skilled in the art will recognize that changes can be made which are within the spirit and scope of the invention as set forth in the appended claims.

We claim:

1. An insect cell infected with a recombinant baculovirus comprising cDNA encoding mammalian calpain I.

2. The insect cell of claim 1 wherein said calpain is human calpain.

3. The insect cell according to claim 1 wherein said baculovirus is *Autographa californica*.

4. The insect cell according to claim 1 wherein said cell is of the species *Spodoptera frugiperda*.

5. An insect cell infected with a recombinant baculovirus comprising cDNA encoding a subunit of mammalian calpain I of about 80 kDa.

6. The insect cell of claim 5 wherein said calpain is human calpain.

7. A recombinant baculovirus having the ATCC designation ATCC VR 2457.

8. A recombinant baculovirus having the ATCC designation ATCC VR 2458.

9. An insect cell of the species *Spodoptera frugiperda* infected with a recombinant baculovirus of the species *Autographa californica*, said baculovirus comprising cDNA encoding mammalian calpain I.

* * * * *

UNITED STATES PATENT AND TRADEMARK OFFICE
CERTIFICATE OF CORRECTION

PATENT NO. : 5,869,336
DATED : February 9, 1999
INVENTOR(S) : Meyer et al.

It is certified that error appears in the above-identified patent and that said Letters Patent is hereby corrected as shown below:

Title page, OTHER PUBLICATIONS,
First column, at Barber, G.N. et al., third line thereof, please delete "ds" and insert -- as -- therefor.

Second column, at Fertig,G. et al., please delete "Biotechniological" and insert -- "Boitechnological -- therefor.
Second column, at Hatanaka, M. et al., second line thereof, please delete "Purificatin" and insert -- Purification -- therefor.

Page 2, first column, at Lee, I.J. et al., second line thereof, please delete "tanscription" and insert -- transcription -- therefor.
Page 2, first column, at Lee, K. et al., please delete "' Ihibition" and insert -- "Inhibition -- therefor.
Page 2, first column, at Patel, G. et al., third line thereof, please delete "potein" and insert -- protein -- therefor.
Page 2, first column, at Saido, T.C. et al., second line thereof, please "activatio" and insert -- activation -- therefor.

Page 2, second column, at Sorimachi, et al., third line thereof, please delete "form" and insert -- from -- therefor.
Page 2, second column, at Towbin, H. et al., second line thereof, please delete "polyacryylamide" and insert -- polyacrylamide -- therefor.
Page 2, second column, at Vernet, T. et al., please delete "o ffunctional" and insert -- of functional -- therefor.
Page 2, second column, at Wippler, J. et al., third line thereof, please delete "withhout" and insert -- without -- therefor.
Page 2, second coulmn, at Delphin, C. et al., please delete " (Jil. 1994)" and insert -- (1994) -- therefor.

Column 7,
Line 44, please delete -- 30 --.

Column 10,
Line 67, please delete "20".

Column 16,
Line 1, please delete "ubunits" and insert -- subunits -- therefor.

Column 17,
Lines 53-54 are part of the same sentence; no paragraph necessary.

UNITED STATES PATENT AND TRADEMARK OFFICE
CERTIFICATE OF CORRECTION

PATENT NO. : 5,869,336
DATED : February 9, 1999
INVENTOR(S) : Meyer et al.

It is certified that error appears in the above-identified patent and that said Letters Patent is hereby corrected as shown below:

Column 19,
Line 3, please delete "Melville" N.Y." and insert -- Melville, N.Y. -- therefor.
Line 24, please delete "kDasubunit" and insert -- kDa subunit -- therefor.

Column 20,
Line 5, please delete "451%" and insert -- 45% -- therefor.

Signed and Sealed this

Twenty-ninth Day of January, 2002

Attest:

*Attesting Officer*

JAMES E. ROGAN
*Director of the United States Patent and Trademark Office*